(12) United States Patent
Hashiguchi et al.

(10) Patent No.: US 7,906,565 B2
(45) Date of Patent: Mar. 15, 2011

(54) TISSUE CONDITIONER FOR DENTAL USE

(75) Inventors: Masanao Hashiguchi, Tokyo (JP); Mitsuhiro Yamashita, Tokyo (JP); Hideki Kazama, Tokyo (JP)

(73) Assignees: Tokuyama Corporation, Shunan-Shi, Yamaguchi (JP); Tokuyama Dental Corporation, Taito-Ku, Tokyo (JP)

( * ) Notice: Subject to any disclaimer, the term of this patent is extended or adjusted under 35 U.S.C. 154(b) by 182 days.

(21) Appl. No.: 11/884,208

(22) PCT Filed: Feb. 2, 2006

(86) PCT No.: PCT/JP2006/302219
§ 371 (c)(1),
(2), (4) Date: Mar. 28, 2008

(87) PCT Pub. No.: WO2006/087961
PCT Pub. Date: Aug. 24, 2006

(65) Prior Publication Data
US 2008/0293011 A1    Nov. 27, 2008

(30) Foreign Application Priority Data
Feb. 15, 2005 (JP) ................................ 2005-038184

(51) Int. Cl.
A61K 6/00 (2006.01)
(52) U.S. Cl. ........................................................ 523/120
(58) Field of Classification Search .................. 523/120, 523/116, 115; 52/25
See application file for complete search history.

(56) References Cited

U.S. PATENT DOCUMENTS

| | | | |
|---|---|---|---|
| 3,637,563 A | 1/1972 | Christena et al. | |
| 3,806,484 A | 4/1974 | Dargan | |
| 4,824,876 A * | 4/1989 | Matsumoto et al. | 522/24 |
| 5,318,999 A * | 6/1994 | Mitra et al. | 522/57 |
| 5,395,862 A | 3/1995 | Neckers et al. | |
| 5,500,454 A * | 3/1996 | Obana et al. | 523/120 |
| 5,639,802 A | 6/1997 | Neckers et al. | |
| 5,663,214 A * | 9/1997 | Okada | 523/120 |
| 5,698,611 A * | 12/1997 | Okada et al. | 523/120 |
| 5,744,511 A | 4/1998 | Kazama et al. | |
| 5,885,837 A | 3/1999 | Winkler et al. | |
| 6,433,037 B1 * | 8/2002 | Guzauskas | 522/71 |
| 6,472,454 B1 * | 10/2002 | Qian | 523/116 |
| 6,506,815 B2 * | 1/2003 | Shinozaki et al. | 522/74 |
| 6,610,759 B1 * | 8/2003 | Chappelow et al. | 522/25 |
| 6,765,036 B2 | 7/2004 | Dede et al. | |
| 6,930,134 B2 | 8/2005 | Suzuki et al. | |
| 7,312,256 B2 * | 12/2007 | Borja | 523/120 |
| 2003/0069326 A1 * | 4/2003 | Stangel et al. | 523/113 |
| 2003/0153645 A1 * | 8/2003 | Sun et al. | 523/116 |
| 2003/0158288 A1 * | 8/2003 | Lehmann et al. | 523/115 |
| 2004/0048948 A1 * | 3/2004 | Yamashita et al. | 523/120 |
| 2004/0186195 A1 | 9/2004 | Suzuki et al. | |
| 2005/0250868 A1 | 11/2005 | Suzuki et al. | |
| 2007/0141267 A1 | 6/2007 | Sonnenschein et al. | |

FOREIGN PATENT DOCUMENTS

| | | |
|---|---|---|
| EP | 0897710 A2 | 2/1999 |
| EP | 0927726 A1 | 7/1999 |
| EP | 1422254 A2 | 5/2004 |
| EP | 1431315 A2 | 6/2004 |
| JP | 02-297358 A | 12/1990 |
| JP | 03-020204 A | 1/1991 |
| JP | 11-130945 A | 5/1999 |
| JP | 2003-327504 A | 11/2003 |
| JP | 2004-196949 | 7/2004 |
| JP | 2005-206471 A | 8/2005 |

OTHER PUBLICATIONS

Minoru Kawaguchi et al., "Factors Affecting the Leaching of Phtalate Esters of the Experimental Tissue Conditioner", Japanese Dentistry Science and Technology Society, 2004, pp. 273-278, vol. 23, No. 4.
Naoyuki Katakura et al., "Tissue Conditioners Containing Poly (butyl methacrylate) Powder I. Viscoelastic Properties of Homopolymer/Plasticizer Mixture", Dental Materials Journal, 1989, pp. 35-39, vol. 8, No. 1.
Hiroshi Murata et al., "Alcohol o Ganyu shinai Shinkaihatsu no Tissue Conditioner no Bussei", Japanese Prosthodontic Society Gakujutsu Taikai Shorokushu, 2001, p. 86, vol. 106.
Noriya Hashimoto et al., "Phthalic Acid Ester-rui Free no Atarashii Menmaku Choseizai no Kaihatsu", Japan Prosthodontic Society Gakujutsu Taikai Shorokushu, 2002, p. 130, vol. 107.

* cited by examiner

*Primary Examiner* — Mark Eashoo
*Assistant Examiner* — David Karst
(74) *Attorney, Agent, or Firm* — Buchanan Ingersoll & Rooney PC

(57) ABSTRACT

A mucosal adjustment material comprising a combination of a powdery material (a) and a liquid material (b), characterized especially in that a noncrosslinked (meth)acrylic polymer powder having a Tg in the range of 0-60° C., e.g., polybutyl methacrylate, is used as the powdery material and a liquid polymer which has a mass-average molecular weight of 1,000-10,000 and in which the content of oligomers having a molecular weight of 500 or lower is 10 mass % or lower is used as the liquid material. Such powdery material and liquid material are kneaded together to prepare a paste, which is applied to a denture base and used as a temporary relining material. This mucosal adjustment material in a paste form is reduced in the amount of ingredients eluted from the material during use in the mouth. In an ordinary use period, the relining material retains its initial flexibility and does not deteriorate the denture base.

7 Claims, No Drawings

TISSUE CONDITIONER FOR DENTAL USE

FIELD OF THE INVENTION

The present invention relates to a tissue conditioner for dental use which, in the treatment of teeth, can be applied to a denture base worn by a patient who has developed a deformation or an inflammation in the oral mucosa in order to maintain fitness between the denture and the mucosa until such deformation or inflammation is cured.

BACKGROUND ART

It has been known that when a denture is used for extended periods of time, the shape of the oral cavity gradually varies due to dissolution of alveolar bone that is forming alveolar ridge into the oral tissue. In such a case, fitness becomes poor between the denture base and the oral mucosa, and the denture loses stability. If the poorly fit denture is continuously used, non-uniform pressure is exerted on the mucosa that comes in contact with the denture. Therefore, an ulcer or an inflammation occurs in the mucosa, and a pain is triggered by the force of occlusion. Therefore, in case such an unfitness has occurred, it becomes necessary to recover the fitness of the denture to the mucosa by preparing a new denture or by relining the denture that is in use.

However, the oral mucosa of a patient who is suffering from a serious ulcer or inflammation is in a very unstable state. Therefore, a favorable fitness must be maintained between the denture base and the mucosa prior to preparing a new denture or relining the denture until the oral mucosa (tissue) recovers to a relatively healthy condition. The tissue conditioner for dental use is used for such a case. Namely, the tissue conditioner for dental use is a therapeutic material used for relining the denture that is now in use until the form and color tone of the mucosa under the denture base are recovered to a normal state.

Soft materials now used in connection with the denture bases can be roughly divided into a paste for fixing the denture base (so-called denture adhesive), a tissue conditioner for dental use and a soft relining material, which are used for different purposes, for different methods, for different periods of time and for providing different properties.

The paste for fixing the denture base is applied by the patient himself for relieving the pain, and is used for only a very short period of time. Use of this material is limited to be only temporarily and is not for the purpose of therapy. The material can be used in a powdery form, in a cream form, in a seal form, and is either water-soluble or water-insoluble. The paste increases the viscosity of saliva and works to increase the adhering force of the denture base to the surface of the mucosa. The water-insoluble paste eliminates the gap between the denture base and the surface of the mucosa to improve fitness, and increases the adsorbing force based on the effect of marginal adaptability. These pastes have almost no elasticity, and undergo a large plastic deformation for each occlusion to a degree that depends upon the pressure of occlusion. Therefore, their use is limited to one day to several days.

On the other hand, the tissue conditioner for dental use and the soft relining material have a common point in that they are applied by a dentist but exhibit properties that are greatly different depending upon the objects of use.

Concretely, the tissue conditioner for dental use (hereinafter often simply called tissue conditioner) is used for the therapy of the oral mucosa in a stage that precedes the repair of denture components as described above. The tissue conditioner is a soft high-molecular material which is applied to the surface of the denture base that comes in contact with the mucosa to release the distortion and indentation of mucosa under the denture base and that varies its state following the displacement of the mucosa. The tissue conditioner is used in the form of a paste formed by mulling a powder and a liquid material together. The paste exhibits a high fluidity at first. As the time elapses, however, the liquid material infiltrates into the powder and viscoelasticity is exhibited. Therefore, the paste is applied onto the surface of the denture base while it still has fluidity, and is inserted in the oral cavity to impart the shape thereto. The period of use is from about several days to about several weeks until the oral mucosa recovers to a healthy condition. The tissue conditioner must not be pushed out from between the denture and the surface of the mucosa at the time of occlusion but must remain flexible and capable of undergoing fine deformation so as to follow the recovery of the oral mucosa yet being held on the surface of the mucosa. If described in further detail, the tissue conditioner is relined onto the surface of the denture base that fits poorly in order to recover the fitness between the denture and the oral mucosa to wait for the gradual diminishing of ulcer and inflammation of the oral mucosa while relieving the pain. As the ulcer and inflammation of oral mucosa gradually diminish, the state of the oral mucosa recovers with the passage of time to resume the original state. Here, the tissue conditioner must undergo the plastic deformation to meet a change in the state of the oral mucosa. This is because, if the tissue conditioner does not undergo the deformation that is described above, the fitness is lost as the state of the oral mucosa recovers creating a factor that causes a pain again.

On the other hand, the soft relining material is a material that is used when the oral mucosa is in a healthy condition. When the ulcer or inflammation is occurring in the oral mucosa, the tissue conditioner is used until the ulcer or inflammation extinguishes, i.e., to wait for the extinction of the ulcer or inflammation. After the ulcer and inflammation have extinguished and the oral mucosa has resumed the healthy condition, the soft relining material is used. Therefore, when neither the ulcer nor the inflammation is occurring, the soft relining material is readily used without using the tissue conditioner. That is, the tissue conditioner is applied to the denture base as a temporary relining material for a period of several days to several weeks until the ulcer or the inflammation extinguishes, whereas the soft relining material is used as a relining material for repairing the denture base when the oral mucosa is in a healthy condition to exhibit its function for at least six months. Therefore, the characteristics of the two are obviously different.

For example, the tissue conditioner is used when the ulcer or the inflammation is occurring, and is very soft. From the standpoint of suitably holding the denture for extended periods of time or from the standpoint of the feeling of use of the denture, however, the tissue conditioner is too soft. Further, the oral mucosa after recovered does not so change as during the stage of from the occurrence of ulcer until the recovery thereof. Therefore, a high degree of plasticity possessed by the tissue conditioner adversely affects the holding of the denture or the feeling of use. Therefore, the soft relining material used for the repaired denture base is a soft material which, however, is slightly harder than the tissue conditioner and does not exhibit such a large plastic deformation as that of the tissue conditioner. Besides, the soft relining material is used for a period of time longer than the tissue conditioner and, therefore, has mechanical properties such as tensile strength and the like which are very higher than those of the tissue conditioner.

As described above, the above three kinds of materials are all soft materials and are used for relining the denture, but are used as clearly different dental materials from the standpoint of their purposes of use and required properties.

As described above, though so high strength is not required, a high degree of softness and plasticity are required for the tissue conditioner. The tissue conditioners of a variety of compositions have been proposed for satisfying the above properties. From the standpoint of simplicity at the time of use, however, many of the tissue conditioners now used are those comprising a (meth)acrylic polymer powder and a liquid material of various plasticizers as chief components (see, for example, non-patent document 1, and patent documents 1 and 2).

The plasticizers are the components necessary for exhibiting softness and plasticity. At present, a phthalate-type plasticizer has been chiefly used. For example, a paste of a powder component comprising a (meth)acrylic polymer powder such as a polyethyl methacrylate or a copolymer thereof and a liquid component comprising a phthalate-type plasticizer containing ethanol in an amount of about 4 to about 30 mass %, has been widely used as a tissue conditioner. The liquid component is, in many cases, blended with ethanol to improve kneading property and property after kneaded.

However, the tissue conditioner using the above plasticizer has a problem in that the plasticizer gradually elutes out (e.g., see non-patent document 1).

Non-patent document 1: "Factors Affecting the Leaching of Phthalic Ester of the Experimental Tissue Conditioner" (N. Kawaguchi and three others), Dental Material and Device, Japanese Society of Dental Materials and Devices, July 2004, Vol. 23, No. 4, pp. 273-278.

Patent document 1: JP-A-3-20204

Patent document 2: JP-A-2-297358

That is, if the plasticizer elutes out, the paste of the tissue conditioner loses viscoelasticity with the passage of time and is cured. The elution occurs in a relatively short period of time of about several days and becomes a serious problem for the tissue conditioner which is used for a period of time shorter than the soft relining material and for which more softness is required than the soft relining material. Therefore, the tissue conditioner had to be renewed every after several days. It has further been suspected that the phthalic acid ester-type plasticizer exhibits estrogen-like action. The plasticizer eluted out from the tissue conditioner infiltrates into the body and may affect the health. Moreover, if the material containing the plasticizer that is left to stand in contact with any other substance, the plasticizer may diffuse and may transform into other substances. Therefore, if the tissue conditioner containing the plasticizer is used in the oral cavity being stuck to the denture base, the plasticizer gradually migrates into the denture base. As a result of migration of the plasticizer, the denture base is softened and is deteriorated.

As a plasticizer to substitute for the phthalate-type ones that may affect health, a sebacate-type plasticizer has recently been used without, however, solving the problems of a decrease in the softness caused by the elution of the plasticizer or the deterioration of the denture base caused by the migration of plasticizer into the denture base.

SUMMARY OF THE INVENTION

It is, therefore, an object of the present invention to provide a tissue conditioner which does not permit the softness to decrease for at least about 4 weeks and which, when applied to the denture base, does not elute components that may deteriorate the denture base.

The present inventors have conducted keen study in an effort to solve the above problems, have discovered the fact that a paste formed by mulling a powdery material together with a liquid polymer having a mass average molecular weight in a range of 1,000 to 10,000 and containing not more than 10 mass % of oligomers having molecular weights of not more than 500, maintains softness with stability and does not cause the denture base to be deteriorated even when it is applied to the denture base, and have finished the present invention based on the above discovery.

According to the present invention, there is provided a tissue conditioner for dental use (dental tissue conditioner) comprising (a) a powdery material and (b) a liquid material which are packed separately from each other and which, at the time of use, are mixtured together so as to be used as a paste thereof, wherein:

the powdery material (a) is a non-crosslinked (meth)acrylic polymer powder having a glass transition temperature in a range of 0 to 60° C.; and the liquid material (b) is a liquid polymer having a mass average molecular weight in a range of 1,000 to 10,000 and containing not more than 10 mass % of oligomers having molecular weights of not more than 500.

In the present invention, the mass molecular weights all stand for molecular weights calculated as a standard polystyrene as measured by the gel permeation chromatography (GPC).

To use the dental tissue conditioner of the present invention, the powdery material (a) and the liquid material (b) are mixed together to form a paste thereof which is, then, applied onto a denture base so as to serve as a temporary relining material. The dental tissue conditioner of the present invention contains no plasticizer that may affect health and elutes little component when used in the oral cavity. Besides, within an ordinarily contemplated period of use, the dental tissue conditioner of the present invention maintains the initial softness and does not cause the denture base to deteriorate.

BEST MODE FOR CARRYING OUT THE INVENTION

The tissue conditioner for dental use of the present invention comprises (a) a powdery material and (b) a liquid material which are separately packed and which, at the time of use, are unpacked and are mixed together so as to be used as a paste thereof.

[Powdery Material (a)]

As the powdery material (a) in the present invention, there is used a powdery polymer (a-1) comprising a non-crosslinked (meth)acrylic polymer having a glass transition temperature (Tg) in a range of 0 to 60° C. In order to adjust various properties, any other powders may be used in combination, such as a crosslinked polymer powder (a-2), a non-crosslinked polymer powder (a-3) having Tg which is higher than 60° C. and an average particle size in a predetermined range, and an inorganic powder (a-4).

Powdery Polymer (a-1).

The powdery polymer (hereinafter often called low-Tg non-crosslinked polymer) must have a glass transition temperature (Tg) in a range of 0 to 60° C. If the polymer has Tg which is lower than 0° C., the polymer particles aggregate together very strongly while the polymer is being preserved at room temperature (environmental temperature at which the tissue conditioner is preserved before being used: about 18 to 35° C.). As a result, a paste is not obtained even when it is mixed together with the liquid material (b) that will be described later. If Tg exceeds 60° C., the product mulled with the liquid material (b) becomes so hard as to spoil the softness (e.g., Shore A hardness of not larger than 20) required for the tissue conditioner. It is desired that Tg of the low-Tg non-crosslinked polymer is in a range of 10 to 50° C. from the standpoint of effectively preventing the aggregation of the powder while being preserved before being used and that the paste formed by being mulled with the liquid material (b) may exhibit more preferred softness as the tissue conditioner.

Further, the powdery polymer (a-1) must assume the form of a paste upon being mulled with the liquid material (b). Therefore, the polymer must be of the non-crosslinked structure. This is because the polymer having the crosslinked structure does not dissolve in the liquid material (b) and does not form a paste.

Moreover, the low-Tg non-crosslinked polymer must be a (meth)acrylic polymer. That is, the (meth)acrylic polymer having Tg in the above range and the non-crosslinked structure exhibits good affinity to the (meth)acrylic denture base and, further, makes it possible to obtain a suitable degree of viscoelasticity.

The (meth)acrylic polymer includes any one of a homopolymer obtained by homopolymerizing a polymerizable monomer ((meth)acrylic monomer) having an acrylic group or a methacrylic group as a polymerizable group, a copolymer obtained by copolymerizing two or more different (meth)acrylic monomers, or a copolymer obtained by copolymerizing a (meth)acrylic monomer and a polymerizable monomer other than the (meth)acrylic monomer (having, however, a ratio of monomer units based on the (meth)acrylic monomer of not less than 50 mol %).

Described below are examples of the (meth)acrylic homopolymer having Tg lying in the above range:

Poly(benzyl acrylate), poly(4-butoxycarbonylphenyl acrylate), poly[3-chloro-2,2-bis(chloromethyl)propyl acrylate], poly(2-chlorophenyl acrylate), poly(4-chlorophenyl acrylate), poly(4-methoxyphenyl acrylate), poly(2,4-dichlorophenyl acrylate), poly(cyclohexyl acrylate), poly(cyclododecyl acrylate), poly(2-methoxycarbonylphenyl acrylate), poly(3-methoxycarbonylphenyl acrylate), poly(2-ethoxycarbonylphenyl acrylate), poly(3-ethoxycarbonylphenyl acrylate), poly(4-ethoxycarbonylphenyl acrylate), poly(heptafluoro-2-propyl acrylate), poly(hexadecyl acrylate), polymethyl acrylate, polyneopentyl acrylate, polyphenyl acrylate, poly(m-tolyl acrylate), poly(o-tolyl acrylate), poly (p-tolyl acrylate), poly(N-butylacrylamide), poly(propyl methacrylate), poly(n-butyl methacrylate), poly(i-butyl methacrylate), poly(neopentyl methacrylate), poly(cyclohexyl methacrylate), poly(hexadecyl methacrylate), poly(octadecyl methacrylate), poly(3-oxabutyl methacrylate), poly (benzyl methacrylate), poly(2-t-butylaminoethyl methacrylate), poly(butylbutoxycarbonyl methacrylate), poly(1H,1H-heptafluorobutyl methacrylate), poly(1H,1H,5H-octafluoropentyl methacrylate) and poly(1H,1H,7H-dodecafluoroheptyl methacrylate).

Described below are examples of the copolymer obtained by copolymerizing (meth)acrylic monomers together:

Poly(methyl methacrylate-n-butyl acrylate), poly(ethyl methacrylate-n-butyl acrylate), poly(propyl methacrylate-n-butyl acrylate), poly(methyl methacrylate-n-butyl acrylate), poly(ethyl methacrylate-n-butyl methacrylate), poly(propyl methacrylate-n-butyl methacrylate) and poly(i-butyl methacrylate-n-butyl methacrylate).

As the copolymer obtained by copolymerizing the (meth) acrylic monomer with other polymerizable monomer, there can be exemplified poly(styrene-n-butyl methacrylate) and the like.

The above variety of copolymers may be random copolymers, alternate copolymers or block copolymers so far as they are in a powdery form having Tg lying in a predetermined range and having a non-crosslinked structure. In the case of the copolymer, Tg can be adjusted by adjusting the copolymerizing ratio or the like, and there may be contained a monomer unit based on a polymerizable monomer of which a homopolymer has a Tg of not lower than 60° C.

Among the above low-Tg non-crosslinked polymers, it is desired to use a non-crosslinked polymer having a monomer unit based on a (meth)acrylic acid ester from the standpoint of solubility and easy handling and, particularly, to use a homopolymer having a monomer unit based on a (meth) acrylic acid ester of an alcohol with 3 to 20 carbon atoms and, more preferably, 3 to 10 carbon atoms (such as poly(propyl methacrylate) or poly(n-butyl methacrylate)) in an amount of 50 to 100 mol % and, more preferably, 80 to 100 mol %, or a copolymer thereof.

There is no particular limitation on the size of the low-Tg non-crosslinked polymer so far as it is in a powdery form. It is, however, desired that the low-Tg non-crosslinked polymer has a volume average particle size in a range of 0.1 to 100 µm, more preferably, 1 to 90 µm and, most preferably, 5 to 50 µm from the standpoint of easy handling of the powder (fluidity, aggregation) and mixing/kneading with the liquid material (b).

There is no particular limitation on the average molecular weight or on the molecular weight distribution of the low-Tg non-crosslinked polymer provided it is in a powdery form. If the average molecular weight is too small, however, the paste thereof obtained by being mixed and kneaded with the liquid material exhibits poor handling property, or Tg thereof becomes lower than 0° C. or the paste turns into a liquid form in extreme cases. On the other hand, the low-Tg non-crosslinked polymer having a very large average molecular weight is difficult to synthesize or to obtain, and, often, makes it difficult to form a paste that can be favorably operated. It is therefore desired that the powdery low-Tg non-crosslinked polymer having a mass average molecular weight in a range of 20,000 to 5,000,000 and, particularly, 50,000 to 1,000,000 is used as the powdery material (a) for forming the tissue conditioner of the invention.

The above powdery low-Tg non-crosslinked polymer (a-1) may be a mixed powder of two or more kinds of powdery polymers having different kinds and ratios of monomer units for constituting the polymer, different average molecular weights and molecular weight distributions, and different average particle sizes.

As described above, the powdery material (a) used in the invention may contain the crosslinked polymer powder (a-2), the non-crosslinked polymer powder (a-3) having Tg of not lower than 60° C. and an average particle size in a predetermined range (hereinafter often called high-Tg non-crosslinked polymer powder) and the inorganic powder (a-4) in addition to the above powdery low-Tg non-crosslinked polymer (a-1). By using these other powders in combination, the paste obtained by being mulled with the liquid material (b) can be adjusted for its properties.

Crosslinked Polymer Powder (a-2).

Upon being blended with the crosslinked polymer powder (a-2) in addition to the above low-Tg non-crosslinked polymer powder (a-1), the paste obtained by mixing and kneading the powder and the liquid is imparted with a favorable initial fluidity. That is, upon mixing and kneading the powdery material and the liquid material, the low-Tg non-crosslinked polymer dissolves in the liquid material component and the viscosity rises. In this case, the crosslinked polymer powder, too, swells due to the liquid material component to exhibit an increased viscosity. However, the rate of an increase of the viscosity thereof is smaller than that of the non-crosslinked polymer. Upon being blended with the crosslinked polymer powder (a-2), therefore, it is allowed to adjust the change in the viscosity (fluidity) of the paste with the passage of time. In the initial stage of preparation, the paste has a low viscosity and an excellent fluidity, and can be easily applied onto the denture base. Thereafter, the viscosity increases to maintain the shape with stability.

There is no particular limitation on the crosslinked polymer so far as it does not hinder the effect of the invention. Generally, however, the (meth)acrylic polymer in which a crosslinked structure is introduced can be preferably used since it does not greatly affect the properties of the paste. Concrete examples of the above crosslinked polymer include those obtained by polymerizing, in the presence of a crosslinking agent, at least one kind of (meth)acrylate monomers such as methyl(meth)acrylate, ethyl(meth)acrylate, propyl(meth)acrylate, isopropyl(meth)acrylate, butyl(meth)acrylate, isobutyl(meth)acrylate, hexyl(meth)acrylate, 2-ethylhexyl(meth)acrylate or cyclohexyl(meth)acrylate. As the crosslinking agent, in this case, there is used the one having two or more unsaturated double bonds, such as divinyl benzene, (poly)ethylene glycol diacrylate compound or (poly)ethylene glycol dimethacrylate, usually, in an amount of about 5 to about 50 parts by weight per 100 parts by weight of the (meth)acrylate monomer.

Though there is no particular limitation, it is desired that the crosslinked polymer powder (a-2) has a volume average particle size of 0.1 to 100 μm and, particularly, 1 to 50 μm from the standpoint of maintaining good knead feeling and touch feeling of the composition (paste) at the time of kneading.

There is no particular limitation on the amount of the crosslinked polymer (a-2) provided it is blended in such an amount that does not hinder the effect of the invention. It is, however, desired that the crosslinked polymer powder (a-2) is used in an amount in a range of 5 to 100 parts by mass and, particularly, 10 to 90 parts by mass per 100 parts by mass of the non-crosslinked polymer powder (a-1) to improve the feeling of kneading the prepared powdery material with the liquid material and to improve softness of the final composition.

As the above crosslinked polymer powder (a-2), there may be used in combination two or more kinds of powdery polymers having different kinds and ratios of monomer units for constituting the polymer, different average molecular weights and molecular weight distributions, and different average particle sizes.

High-Tg Non-Crosslinked Polymer Powder (a-3).

The above-mentioned low-Tg non-crosslinked polymer powder (a-1) having Tg of not higher than 60° C. tends to be aggregated while it is preserved due to its low Tg, becomes difficult to takeout from the preservation container, and tends to be less mixed and kneaded with the liquid material (b). To prevent such an aggregation, therefore, it is desired in this invention to use the high-Tg non-crosslinked polymer powder (a-3) in combination. That is, the high-Tg non-crosslinked polymer powder is a powdery polymer having Tg which is higher than 60° C. and a volume average particle size of not larger than 1 μm (hereinafter often called simply a "high-Tg polymer"). If the average particle size exceeds 1 μm, it often becomes difficult to obtain an aggregation-suppressing effect to a sufficient degree.

Though there is no particular limitation, the high-Tg non-crosslinked polymer may be, generally, the one having of not higher 60° C. among those (meth)acrylic polymers exemplified for the low-Tg non-crosslinked polymer powders (a-1) from the standpoint of chemical stability and transparency. Among them, particularly preferred examples are the poly (methyl methacrylate) and poly(ethyl methacrylate) having compositions resembling the polymer that constitutes the denture base.

The high-Tg non-crosslinked polymer powder (a-3) is blended in an amount in a range of 0.01 to 30 parts by mass and, particularly, 0.1 to 20 parts by mass per 100 parts by mass of the low-Tg non-crosslinked polymer powder (a-1) from the standpoint of kneading.

In present invention, the high-Tg non-crosslinked polymer powder (a-3) and the crosslinked polymer powder (a-2) are used being mixed with the low-Tg non-crosslinked polymer powder (a-1) to prevent the aggregation of the powdery material (a), and are, at the same time, mulled with the liquid material (b) to improve the initial fluidity (operability) of the paste that is prepared. When the powder (a-3) and the powder (a-2) are used as described above, it is desired that the total amount thereof does not exceed 100 parts by mass per 100 parts by mass of the low-Tg non-crosslinked polymer powder (a-1).

As the above high-Tg non-crosslinked polymer powder (a-3), there may be used in combination two or more kinds of powdery polymers having different kinds and ratios of monomer units for constituting the polymer, different average molecular weights and molecular weight distributions, and different average particle sizes.

Inorganic Powder (a-4).

In the present invention, the powdery material (a) is further blended with an inorganic powder (a-4) in an attempt to adjust the hardness of the paste that is prepared by being mulled with the liquid material (b) that will be described later. That is, the inorganic powder (a-4) is used in combination with the low-Tg non-crosslinked polymer powder (a-1) to increase the hardness of the paste that is applied to the denture base. The final hardness of the paste that is formed may often become too soft depending upon the composition of the powdery material (a) that is set from the standpoint of preservation stability, kneading property and economy, and upon the ratio of amounts of the powdery material (a) and the liquid material (b). In such a case, the inorganic powder (a-4) is used to increase the final hardness of the paste to a hardness suited as a tissue conditioner (Shore A hardness of 5 to 20 and, particularly, about 10 to about 20).

There is no particular limitation on the inorganic powder which, therefore, is selected out of those which are usually used as reinforcing materials or fillers in the resin compositions. Concretely, there can be exemplified calcium carbonate, calcium sulfate, magnesium oxide, barium carbonate, barium sulfate, titanium oxide, potassium titanate, barium titanate, aluminum hydroxide, magnesium hydroxide, silicon powder, glass powder, diatomaceous earth, silica, calcium silicate, talc, alumina, bentonite, zeolite, kaolin clay, mica and quartz glass, which may be used in one kind or in a combination of two or more kinds. From the standpoint of easy handling, affinity to the liquid material (b) and dissolution (elution) in the saliva, however, silica or alumina is preferably used. From the standpoint of easy availability, the fumed silica is most desired.

There is no particular limitation on the particle size of the above inorganic powder. From the standpoint of preservation stability and kneading, however, it is desired that the inorganic powder has a volume average particle size of not larger than 1 μm and, particularly, not larger than 0.1 μm. There is no particular limitation on the amount of use so far as the properties of the tissue conditioner are not impaired and a suitable degree of hardness is exhibited. Generally, however, the inorganic powder is used in an amount of 0.001 to 5 parts by mass and, particularly, 0.01 to 2 parts by mass per 100 parts by mass of the low-Tg non-crosslinked polymer (a-1) from the standpoint of knead feeling of the powdery material (a) and the liquid material (b).

The inorganic powder (a-4) is usually blended in the powdery material (a) from the standpoint of preservation stability and the kneading property. Depending upon the cases, however, the inorganic powder (a-4) may have been entirely or partly blended in the liquid material (b).

[Liquid Material (b)]

The tissue conditioner for dental use of the present invention uses a liquid polymer as a liquid material (b) for forming the paste being kneaded with the powdery material (a). In the present invention, liquid stands for that the liquid material is in a liquid state in a temperature range of from room temperature to a temperature in the oral cavity, i.e., from 18 to 40° C. If the liquid material is not in the liquid state in the above temperature range, the paste is not prepared or the paste does not exhibit a suitable degree of viscoelasticity despite the liquid material is kneaded with the above powder material (a).

The liquid polymer must not be soluble in water to avoid the elution in the oral cavity, and its solubility in water at 37° C. which is an average temperature in the oral cavity is not larger than 5 mass %, particularly, not larger than 3 mass % and, most desirably, not larger than 1 mass %. In the present invention, it is important that the liquid polymer has a mass average molecular weight and an oligomer content lying within predetermined ranges.

That is, the mass average molecular weight of the liquid polymer is in a range of 1,000 to 10,000. If the mass average molecular weight is less than 1,000, the polymer easily elutes out in an environment such as in the oral cavity, and the paste applied to the denture base loses its viscoelasticity and the softness within relatively short periods of time. On the other hand, if the mass average molecular weight exceeds 10,000, a suitable degree of softness cannot be imparted, and the liquid polymer cannot be used as the tissue conditioner. It is, further, difficult to obtain a polymer which is in the liquid form and has a mass average molecular weight in excess of 10,000. In the present invention, it is desired that the liquid polymer has a mass average molecular weight in a range of 1,200 to 7,000 and, particularly, 1,500 to 5,000 from the standpoint of kneading of the liquid polymer and the above powdery material (a).

In the liquid polymer, further, the content of the oligomer having a molecular weight of not larger than 500 must be suppressed to be not larger than 10 mass %, particularly, not larger than 7 mass % and, most desirably, not larger than 5 mass %. If the oligomer component of a low molecular weight is contained in large amounts, the oligomer component easily elutes out in the oral cavity to spoil the viscoelasticity and softness of the paste and, further, permitting the oligomer component to easily migrate into the denture base which is, therefore, damaged.

It is further desired that the liquid polymer component having a molecular weight in excess of 10,000 is smaller than 10 mass % and, particularly, smaller than 5 mass %. As the molecular weight increases, in general, the compatibility with other components decreases. If components having large molecular weights are contained in large amounts, it becomes difficult to prepare a paste of a homogeneous composition.

In the present invention, the liquid polymer having the above molecular weight distribution is used as the liquid material (b) that is to be kneaded with the powdery material (a) making it possible to prepare a paste having a suitable viscoelasticity for use as the tissue conditioner, maintaining softness for extended periods of time even when the paste is held in the oral cavity, effectively preventing such an inconvenience that the component in the paste migrates into the denture base, and without damaging the denture base.

There is no limitation on the material of the liquid polymer so far as the condition of the above molecular weight distribution is satisfied. It is, however, desired to use the liquid polymer having good affinity (compatibility) to the low-Tg non-crosslinked polymer powder (a-1) used as the powdery material (a) from the standpoint of obtaining excellent kneading property and excellent properties of the obtained paste. An index that represents the compatibility between the liquid polymer and the low-Tg crosslinked polymer powder can be represented by an increase in the viscosity when the above two materials are mixed together to form a paste. The paste that exhibits a quickly rising viscosity immediately after it is inserted in the oral cavity after the two materials have been mulled together, means that the compatibility is high between the two materials. Concretely speaking, the liquid polymer is mixed with the low-Tg non-crosslinked polymer powder (a-1) in an amount of 1.1 mass times as much, and the two are kneaded together to obtain a homogeneous paste thereof. By using a dynamic viscoelasticity measuring apparatus (CS rheometer), the above paste just prepared is measured for its viscosity under the conditions of a Shore rate of 10 (1/sec) and a measuring temperature (plate temperature) of 37° C. It is desired to use the paste having a viscosity after 300 seconds of not smaller than 1,000 Pas and, more preferably, not smaller than 3,000 Pas.

From the standpoint of obtaining good compatibility, the liquid polymer is selected out of the (meth)acrylic polymers and is, desirably, a (meth)acrylate polymer particularly, from the standpoint of obtaining a liquid polymer having a molecular weight in the above range. The (meth)acrylic polymer that forms the liquid polymer is synonymous to various (meth)acrylic polymers used for forming the powdery material (a), but is different from these used for forming the powdery material (a) with respect to that the average molecular weight thereof and the molecular weight distribution such as oligomer content lie in predetermined ranges and that the polymer is in the liquid form.

There is no particular limitation on the method of producing the liquid polymer used as the liquid material (b), and the liquid polymer produced by any known method can be used without any particular limitation. Typically, the (meth)acrylic monomer may be polymerized, or the (meth)acrylic monomer may be polymerized with other monomer capable of being copolymerized with the (meth) acrylic monomer in a manner that the mass average molecular weight thereof lies in a predetermined range.

As the (meth)acrylate suited as the (meth) acrylic monomer for obtaining the above liquid polymer, there can be exemplified methyl(meth)acrylate, ethyl(meth)acrylate, propyl(meth)acrylate, isopropyl(meth)acrylate, butyl(meth)acrylate, isobutyl(meth)acrylate, hexyl(meth)acrylate, 2-ethylhexyl(meth)acrylate, cyclohexyl(meth)acrylate, glycidyl(meth)acrylate, methoxyethyl(meth)acrylate, ethoxymethyl(meth)acrylate and methoxypropyl(meth)acrylate. As other monomers capable of being copolymerized with the (meth)acrylate monomers, there can be exemplified vinyl acetate, styrene and the like. In this case, one or two or more kinds of (meth)acrylate monomers and one or more kinds of other copolymerizable monomers are polymerized together, and the obtained copolymer can be used as a liquid polymer. From the standpoint of solubility and swelling property, however, it is desired that the liquid polymer contains a monomer unit based on the (meth)acrylate monomer in an amount of not less than 50 mol % and, preferably, not less than 80 mol %.

In the present invention, in particular, at least the one kind of the (meth)acrylate monomer is used being selected from the group consisting of ethyl(meth)acrylate, propyl(meth)acrylate, isopropyl(meth)acrylate, butyl(meth)acrylate, 2-ethylhexyl(meth)acrylate, methoxyethyl(meth)acrylate, ethoxymethyl(meth)acrylate and glycidyl(meth)acrylate from the standpoint of good compatibility with the (meth)acrylic powdery non-crosslinked polymer (a-1) used as the powdery material (a). The above (meth)acrylate monomer is polymerized or is copolymerized with other monomer to obtain a homopolymer or a copolymer thereof to particularly preferably use it as the liquid polymer.

In the present invention, concrete examples of the (meth)acrylate polymer that is particularly suited as the liquid polymer are as follows:

Polyethyl(meth)acrylate, polypropyl(meth)acrylate, polyisopropyl(meth)acrylate, polybutyl(meth)acrylate, poly[2-ethylhexyl(meth)acrylate], poly[ethyl(meth)acrylate-butyl(meth)acrylate], poly[ethyl(meth)acrylate-2-ethylhexyl(meth)acrylate], poly[ethyl(meth)acrylate-methoxyethyl(meth)acrylate], poly[ethyl(meth)acrylate-glycidyl(meth)acrylate], poly[butyl(meth)acrylate-methoxyethyl(meth)acrylate] and poly[butyl(meth)acrylate-glycidyl(meth)acrylate].

The above liquid polymers can be used in a single kind or in a combination of two or more kinds so far as the mass average molecular weight and the oligomer content thereof are within the above-mentioned predetermined ranges.

The liquid polymer which comprises the above monomer unit and has the mass average molecular weight and the oligomer content lying within the predetermined ranges is obtained by a general polymerization reaction, i.e., produced by conducting the polymerization while controlling the blending ratio of the monomer and the polymerization initiator. As polymerization means, there can be preferably used an ionic polymerization or a living radical polymerization which makes it easy to control the average molecular weight. In particular, the anionic polymerization makes it possible to obtain a liquid polymer having a very sharp molecular weight distribution and is close to a monodispersion of a ratio of mass average molecular weight/number average molecular weight which is not larger than 2 inmost of the cases, and makes it easy to satisfy the condition of not including polymers of molecular weights of not larger than 500.

It is desired that the liquid material (b) used in the present invention is blended with a water-soluble organic solvent in addition to the above liquid polymer. Upon being blended with the water-soluble organic solvent, the liquid material (b) exhibits improved fluidity facilitating the handling and, further, improving the kneading property when kneaded with the powdery material (a). The paste that is prepared by the kneading, too, exhibits improved initial fluidity. The improvement in the property presumably stems from the improved permeability and affinity of the liquid polymer that dissolves and swells the (meth)acrylic powdery polymer in the powdery material (a) owing to the water-soluble organic solvent. The tissue conditioner of the invention is used in the oral cavity for relatively extended periods of time. Therefore, it is not desired to use a non-water-soluble organic solvent that may be harmful to the human body.

Concrete examples of the water-soluble organic solvent include alcohols such as ethanol, isopropyl alcohol and isobutyl alcohol; ketones such as methyl ethyl ketone and acetone; and amines such as diethanolamine and triethanolamine. From the standpoint of good/harm to the living bodies and odor, it is desired to use alcohols such as ethanol or isopropylalcohol and it is particularly desired to use ethanol.

There is no particular limitation on the amount of blending the water-soluble organic solvent provided it is in a range in which the effect of the invention can be obtained. From the standpoint of handling the paste, odor, avoiding a change in the properties after eluted from the paste and maintaining good operation feeling, it is desired that the water-soluble organic solvent is used in an amount in a range of 1 to 30 parts by mass and, particularly, 3 to 20 parts by mass per 100 parts by mass of the liquid polymer.

[Other Components]

As required, further, the dental tissue conditioner of the invention may be blended with coloring materials such as dyes and pigments, as well as additives such as perfume, antibacterial agent and antifungal agent. These additives can be added to either the powdery material (a) or the liquid material (b). When they are solids which are insoluble in the liquid polymer, however, the additives are added in the form of powders to the powdery material (a). The coloring materials are added in the form of powders to the powdery material (a) from the standpoint of dispersion when the paste is prepared and the preservation stability.

In the tissue conditioner of the present invention, the liquid material (b) may be blended with a low-molecular compound having a molecular weight of not larger than 500, such as phthalic acid diester plasticizer or sebacic acid diester plasticizer, or with a non-volatile component having a molecular weight of not smaller than 10,000 for adjusting the paste. Such a component, however, is highly probable to gradually elute out and migrate into the denture base to hinder the effect of the invention. Besides, without being blended with the above carboxylic acid diester plasticizer, the tissue conditioner of the invention makes it possible to adjust the paste to possess a sufficient degree of softness and hardness. Therefore, the above component must be suppressed to be not larger than 10 mass %, particularly, not larger than 7 mass % and, most desirably, not larger than 5 mass % per the total amount of the paste obtained by mixing the powdery material (a) and the liquid material (b) together.

[Use of the Dental Tissue Conditioner]

The dental tissue conditioner of the invention comprises the powdery material (a) and the liquid material (b) which are preserved in separate packages. At the time of use, the two are kneaded together to prepare a paste thereof which is, then, applied to the denture base so as to be used as a temporary relining material for short periods of time.

The ratio of mixing the powdery material (a) and the liquid material (b) is so set that a suitable degree of viscoelasticity and the initial fluidity are maintained. Though it may differ depending upon the compositions of the powdery material (a) and the liquid material (b), the mixing ratio is, usually, such that the amount of the liquid polymer in the liquid material (b) is in a range of 50 to 300 parts by mass and, particularly, 80 to 250 parts by mass per 100 parts by mass of the low-Tg non-crosslinking polymer (a-1) in the powdery material (a). If there is a large difference between the amount of the powdery material (a) and the amount of the liquid material (b), a paste is not often formed despite the two are mixed together. From such a point of view, therefore, it is most desired to knead the powdery material (a) and the liquid material (b) at a mass ratio (a/b) in a range of 0.5 to 2.5 and, particularly, 0.8 to 2.0.

The thus formed past is applied onto the denture base and is held in the oral cavity for a predetermined period of time to impart a predetermined shape thereto so as to work as the tissue conditioner.

According to the present invention, the paste of the tissue conditioner adheres less strongly to the methacrylic (e.g., polymethyl methacrylate) denture base than the known tissue conditioner. Prior to applying, therefore, it is desired to apply a suitable adhesive to the surface of the denture base onto where the paste is to be applied. This makes it possible to strongly adhere the paste of the tissue conditioner and the denture base together.

According to the study by the present inventors, though there is no particular limitation, it is particularly desired to use, as the adhesive, an organic solvent solution which contains 0.5 to 30 mass % of a polymer (hereinafter called (meth) acrylic copolymer) which has both a monomer unit based on a methyl methacrylate and a monomer unit based on a (meth) acrylate of alcohols with not less than 3 carbon atoms.

Though the mechanism of effective adhesion between the methacrylic denture base and the paste of the dental tissue conditioner of the present invention has not been clarified yet, it is presumed that upon using the above adhesive, the methyl methacrylate unit in the (meth)acrylic copolymer in the above copolymer entangles with the denture base and the (meth) acrylate unit of alcohols with not less than 3 carbon atoms entangles with the paste of the tissue conditioner, enabling the denture base and the paste to be favorably adhered together. That is, the (meth)acrylic copolymer in the above adhesive has both the methyl methacrylate unit and the (meth)acrylate unit of alcohols with not less than 3 carbon atoms and, therefore, exhibits a very higher adhering strength than when there is used a copolymer or a homopolymer without containing the methyl methacrylate monomer unit, a homopolymer of methyl methacrylate, or a copolymer of methyl methacrylate and ethyl(meth)acrylate [i.e., (meth)acrylate of an alcohol with 2 carbon atoms].

In the (meth) acrylic copolymer used as the adhesive, the (meth)acrylate of an alcohol with not less than 3 carbon atoms may be any known ones. It is, however, difficult to obtain the (meth)acrylate of an alcohol having larger than 20 carbon atoms. Besides, as the monomer unit based on the above (meth)acrylate increases, the (meth)acrylic copolymer dissolves less in the solvent and makes it difficult to prepare a solution that can be applied to the denture base. As the (meth) acrylate of alcohols with not less than 3 carbon atoms, therefore, it is desired to use a (meth)acrylate of alcohols with 3 to 20 carbon atoms.

Described below are concrete examples of the (meth)acrylate of alcohols with 3 to 20 carbon atoms:

N-propyl(meth)acrylate, i-propyl(meth)acrylate, n-butyl (meth)acrylate, i-butyl(meth)acrylate, t-butyl (meth)acrylate, pentyl(meth)acrylate, hexyl(meth)acrylate, octyl(meth)acrylate, 2-ethylhexyl(meth)acrylate, decyl (meth)acrylate, lauryl (meth)acrylate, hexadecyl (meth)acrylate, octadecyl(meth) acrylate, methoxyethyl (meth)acrylate, ethoxymethyl(meth) acrylate, methoxybutyl (meth)acrylate, and hydroxypropyl (meth)acrylate.

Among them, it is desired to use the (meth)acrylate of alcohols with 3 to 10 carbon atoms and, more preferably, the (meth)acrylate of alcohols with 3 to 5 carbon atoms from the standpoint of easy preparation, easy availability and easy synthesis of the solution. Particularly preferably, an n-butyl (meth)acrylate and an i-propyl acrylate can be used. Further, the (meth)acrylic copolymer may contain two or more kinds of monomer units based on the (meth)acrylate of an alcohol of not less than 3 carbon atoms.

There is no particular limitation on the ratio (copolymerizing ratio) of the methyl methacrylate monomer unit ($\alpha$) and the (meth)acrylate monomer unit ($\beta$) of the alcohol with not less than 3 carbon atoms in the (meth)acrylic copolymer. Desirably, however, the ratio (copolymerizing ratio) is, as a molar ratio, in a range of $\alpha:\beta=10:90$ to $80:20$ and, particularly, $15:85$ to $75:25$ from the standpoint of attaining both sufficient degree of initial adhesion and easiness of removal. In addition to containing the above two kinds of monomer units, the copolymer may further contain any other monomer units in a range in which they do not impair the effect. The ratio of the other monomer units is desirably not larger than 20 mol %, particularly not larger than 10 mol % and, most desirably, not larger than 5 mol % of the whole amount.

There is no particular limitation on the arrangement of copolymerization in the copolymer, and any one of random copolymer, block copolymer or graft copolymer may be selected. However, the random copolymer is desired from the standpoint of easy production.

There is no particular limitation on the molecular weight of the (meth) acrylic copolymer provided it is in a range in which the copolymer dissolves in an organic solvent. From the easiness of synthesis and solubility in the inorganic solvent, however, it is desired that the (meth)acrylic copolymer has a mass average molecular weight of 50,000 to 1,000,000 and, particularly, 100,000 to 800,000.

The above (meth)acrylic copolymer used as the adhesive component can be produced by any production method, and can typically be easily obtained by copolymerizing the methyl (meth)acrylate with the (meth)acrylate of alcohols with not less than 3 carbon atoms according to a known method. It can be further obtained in the market.

The (meth)acrylic copolymer is either a solid or a very highly viscous liquid near room temperature and must be used in the form of an organic solvent solution by being dissolved in an organic solvent so as to be applied to the denture base. To attain both a suitable degree of applicability and adhesion, further, it is desired that the concentration of the copolymer in the organic solvent solution is 0.5 to 30 mass %.

There is no particular limitation on the above organic solvent if it is capable of dissolving the copolymer. Concrete examples include hydrocarbon compounds such as hexane, heptane and pentane; aromatic hydrocarbon compounds such as toluene and xylene; alcohol compounds such as ethanol, 1-propanol, 2-propanol, 1-butanol and 2-butanol; ether compounds such as diethyl ether, tetrahydrofuran and t-butylmethyl ether; ketone compounds such as acetone, methyl ethyl ketone and methyl isobutyl ketone; and ester compounds such as ethyl formate, methyl acetate, methyl acetate, propyl acetate and isopropyl acetate, which are non-halogen type organic solvents. These solvents may be used in a single kind or being mixed together in two or more kinds in the form of a mixed solvent. According to the Pharmaceuticals Council No. 307, "Guideline for Residual Solvents in Pharmaceuticals" notified to the metropolis and districts from the Ministry of Health and Welfare in Japan in 1998, the residual solvents in the pharmaceuticals are grouped into three classes 1 to 3 depending upon the toxicity. From the viewpoint of safety, therefore, the material for adjusting the adhesion to be used in the invention must be an organic solvent that belong to neither the class 1 nor the class 2.

Further, among the above-mentioned non-halogen type organic solvents, it is particularly desired to use those having boiling points in a range of 20 to 150° C. since they dry quickly and are easy to handle. From the above standpoint, it is most desired to use ethyl acetate, acetone, ethyl methyl ketone or propyl acetate among them.

The above adhesive comprising an organic solvent solution of the (meth)acrylic copolymer is used for applying the tissue conditioner of the present invention to the methacrylic denture base. There is no particular limitation if the methacrylic denture base is a known one. The methacrylic denture base generally comprises chiefly a poly(methyl methacrylate) being partly copolymerized with an ethyl methacrylate or a styrene and is often crosslinked using a crosslinking agent such as ethylene glycol dimethacrylate.

Prior to applying the tissue conditioner of the present invention, the above adhesive is applied to the surface of the methacrylic denture base. After volatile components such as the organic solvent and the like are removed and dried, a paste of the tissue conditioner of the invention is applied thereto and is held in the oral cavity, so that the paste of the tissue conditioner adheres to the denture base.

As will be understood from the foregoing description, the dental tissue conditioner of the present invention can be placed in the market in the form of a dental tissue conditioner kit in combination with the above-mentioned adhesive.

As described already, the paste of the tissue conditioner of the invention undergoes a small change in the hardness thereof with the passage of time. Therefore, the lining thereof does not have to be frequently renewed unlike that of the conventional tissue conditioner. After the oral mucosa has recovered to a healthy condition, however, the tissue conditioner of the invention must be removed for effecting the permanent relining for the denture base. Though there is no particular limitation on the method of removal in this case, it is desired to use a peeling agent that is described below. Use of the peeling agent makes it very easily to remove the tissue conditioner of the invention from the denture base. As described earlier, the tissue conditioner of the present invention does not permit the plasticizer to migrate unlike the conventional tissue conditioner. Therefore, the surface of the denture base is not coarsened even after the tissue conditioner of the invention is peeled off.

As the peeling agent used for removing the paste of the tissue conditioner of the present invention that is adhered to the denture base by using the above-mentioned adhesive, there can be preferably used a homogeneous solution of water and the organic solvent. In particular, the content of water is 30 to 60 mass % per the total amount of the water and the organic solvent. With the organic solvent only, the denture base often dissolves and its surface is coarsened. It is further desired that the solution contains no water-insoluble organic solvent. As the organic solvent (water-soluble organic solvent) used for the peeling agent, there can be concretely exemplified acetone, ethanol or isopropyl alcohol.

The peeling agent is directly applied to the boundary portion between the paste of the tissue conditioner and the denture base so as to infiltrate therein. The paste of the tissue conditioner can, then, be easily peeled off. After the paste of the tissue conditioner is thus peeled off, the relining is effected by using a denture base relining material according to an established method.

EXAMPLES

The invention will now be concretely described by way of Examples to which only, however, the invention is in no way limited. In Examples and Comparative Examples, properties were evaluated in accordance with the following methods.
(1) Measurement of Glass Transition Point (Tg).

The glass transition point Tg was measured by using a differential scanning calorimeter (DSC 6200 manufactured by Seiko Co.). The temperature was, first, elevated at a rate of 10° C./10 min. until the temperature became higher by about 30° C. than an expected Tg, maintained at that point for 5 minutes, lowered at a rate of 50° C./min., and was quickly elevated again. Temperatures were found at intersecting points of three tangential lines of the obtained signals, and a temperature between these points was regarded to be Tg.
(2) Measurement of Hardness.

The Shore A hardness which is an index of the softness was measured in compliance with JIS-K7215 (Durometer, type A). The powdery material and the liquid material were kneaded together to obtain a paste thereof. Measurement was taken after the paste was left to stand still overnight at 37° C. and, further, after the paste was maintained at 37° C. being immersed in water for one month.
(3) Measurement of Flexural Strength of the Denture Base.

An acrylic plate (50×50×2 mm) prepared by using a denture base resin material (Acron, manufactured by GC Co.) was polished by using a water-resistant polishing paper #800. The paste of the tissue conditioner was held between the two pieces of polished acrylic plates such that the thickness was 2 mm, and was immersed and preserved in water maintained at 37° C. for one month. Thereafter, the paste of the tissue conditioner was removed, was cut into short strips measuring 50×10×2 mm, and was put to a three-point flexural testing by using the Autograph (AG-1, manufactured by Shimazu Mfg. Co.).

For comparison, the acrylic plates without holding the paste of the tissue conditioner therebetween were put to the three-point flexural testing to obtain a value (initial value) of 120 MPa.
(4) Evaluation of Adhesion.

The adhesive was applied to the acrylic plate (Acron, manufctured manufactured by GC Co.) of which the surface has been polished by using a water-resistant polishing paper #800 while pouring water, and a paste obtained by kneading the powdery material (a) and the liquid material (b) of the tissue conditioner at a mass ratio of 1.1 (a/b) was applied onto the above acrylic plate by using a mold of 20×20×1 mm. In this state, the paste was left to stand at 37° C. for 10 minutes to evaluate the adhering force. Concretely, it was attempted to peel the paste of the tissue conditioner from the interface of the paste and the acrylic plate by using a spatula, and a manner of breakdown at that moment was observed and evaluated.

The evaluation was made on the basis of the following three steps A to C:

A: 100% aggregation breakdown of the tissue conditioner (adhering force is strong).
B: Mixed breakdown of the aggregation breakdown and the interfacial breakdown (adhering force is weak).
C: Interfacial breakdown (no adhering force).

Further, the adhesion samples prepared by the above method were preserved being immersed in water maintained at 37° C. for one month and were similarly evaluated for their adhering forces.
(5) Measurement of Time for Kneading the Powdery Material (a) and the Liquid Material (b) Together.

1.1 Mass times of the powdery material (a) was added into a rubber cup into which the liquid material (b) has been introduced being weighed in advance, and the two materials were continuously kneaded by using a spatula until the added powdery material became adapted to the liquid material to turn into a paste thereof. The time was measured from the start of the kneading until a homogeneous paste was obtained, and was regarded to be a kneading time.
(6) Measurement of the Initial Viscosity of the Paste.

Measured by using a dynamic viscoelasticity measuring apparatus, CS rheometer "CVO120HR", manufactured by Bohlin Co. Measurement was taken by using a cone of a diameter of 20 mm and 1° under the conditions of a measuring temperature (plate temperature) of 23° C. and a Shore rate 10

(1/sec). Measured in compliance with the method described in (5) above which states the method of measuring the time for kneading the powdery material (a) and the liquid material (b). The viscosity 30 seconds after a moment (kneaded) when the homogeneous paste was obtained was regarded to be the initial viscosity.

(7) Viscosity Related to the Compatibility Between the Liquid Polymer and the Low-Tg Non-Crosslinked Polymer Powder.

1.1 Mass times of the low-Tg non-crosslinked polymer powder was added into a rubber cup into which the liquid polymer has been introduced being weighted in advance, and the two materials were kneaded by the same method as the one described in (5) above which states the method of measuring the time for kneading the powdery material (a) and the liquid material (b). The viscosity 300 seconds after a moment when the homogeneous paste was obtained was measured by using the dynamic viscoelasticity measuring apparatus, CS rheometer, by the same method as the one described in (6) above which states the method of measuring the initial viscosity of the paste (however, the measuring temperature (plate temperature) was set to be 37° C.).

(8) Volume Average Particle Size.

Measured by using an instrument LS230 manufactured by Beckmann-Coulter Co. Water was used as a dispersant. Prior to taking the measurement, the treatment was conducted with ultrasonic waves for not less than 3 minutes and, thereafter, the measurement was quickly taken.

(9) Evaluation of the Preservation Stability.

Evaluated in terms of a change in the volume average particle size before and after the preservation of the powdery material (a) that was prepared. That is, 100 g of the prepared powdery material (a) was charged into a polypropylene bottle. By attaching a cap thereto, the bottle was left to stand still in an incubator maintained at 37° C. for 3 months. The average particle sizes were compared before and after left to stand still, and were used as indexes of preservation stability.

As the change in the average particle size increases, take out of the powdery material (a) from the bottle varies meaning that the preservation stability becomes poor.

The following compounds were used in Examples and in Comparative Examples.

1. Powdery Material (a):

[Non-Crosslinked Polymer (a-1)]

Non-crosslinked polymers (a-1) which are chief components in the powdery material (a) used in Examples and in Comparative Examples are as shown in Table 1 below. In Table 1, PEMA and POMA are non-crosslinked polymers lying outside the range of Tg required by the low-Tg non-crosslinked polymers (a-1) of the present invention, and are used in Comparative Examples.

Among the non-crosslinked polymers shown in Table 1, PHDMA was synthesized according to the following production example 1, PTMHMA was synthesized according to the following production example 2, and POMA that was used for comparison was synthesized according to the following production example 3.

Production Example 1

Synthesis of PHDMA

Into a three neck distillation flask were introduced: 31.1 g (100 mmol) of a hexadecyl methacrylate, 0.02 g of an azobisisobutylonitrile (AIBN) and 20 ml of toluene, and a nitrogen gas was continuously flown at a rate of 5 ml/min. for 2 hours. After the flow of the nitrogen gas was discontinued, an oil bath was attached and the stirring was continued at a bath temperature of 70° C. for 6 hours. Next, the reaction product was introduced into 10 times amount of methanol, and the formed precipitate was recovered and was washed with methanol. The obtained precipitate was dissolved in benzene, freeze dried, and 18.6 g of the residue was recovered (yield, 60%).

Through the GPC measurement, it was learned that the above residue possessed a mass average molecular weight of 230,000 (calculated as polystyrene) and Mw/Mn=1.80. The obtained solid was pulverized by using a freeze pulverizer (linlex mill manufactured by Hosokawa Micron Co.) to prepare a powder having a volume average particle size of 80 μm.

Production Example 2

Synthesis of PTMHMA

The operation was carried out in the same manner as in the production example 1 but using 21.2 g (100 mmol) of a 3,5,5-trimethylhexyl methacrylate instead of the hexadecyl methacrylate, and 11.7 g of a residue was recovered (yield, 55%).

Through the GPC measurement, it was learned that above the residue possessed a mass average molecular weight of 250,000 (calculated as polystyrene) and Mw/Mn=1.83. The obtained solid was pulverized by using the freeze pulverizer (linlex mill manufactured by Hosokawa Micron Co.) to prepare a powder having a volume average particle size of 80 μm.

TABLE 1

| Abbreviation | Kind | Mass ave. mol. wt. | Glass transition temp. (Tg) | Vol. ave. ptcl. size | Available from |
| --- | --- | --- | --- | --- | --- |
| PBMA | poly(n-butyl methacrylate) | 260,000 | 20° C. | 40 μm | Negami Kogyo Co., D200B |
| PiBMA | poly(i-butyl methacrylate) | 280,000 | 56° C. | 90 μm | Negami Kogyo Co., M0603 |
| PHDMA | poly(hexadecyl methacrylate) | 230,000 | 15° C. | 80 μm | synthesized according to production ex. 1 below |
| PTMHMA | poly(3,5,5-trimethylhexyl methacrylate) | 250,000 | 5° C. | 80 μm | synthesized according to production ex. 2 below |
| PEMA | poly(ethyl methacrylate) | 500,000 | 65° C. | 35 μm | Negami Kogyo Co., EMA-35 |
| POMA | poly(n-octyl methacrylate) | 220,000 | −20° C. | — | synthesized according to production ex. 3 below |

Production Example 3

Synthesis of POMA

The operation was carried out in the same manner as in the production example 1 but using 19.8 g (100 mmol) of an n-octyl methacrylate instead of the hexadecyl methacrylate, and 10.9 g of a residue was recovered (yield, 55%).

Through the GPC measurement, it was learned that the above residue possessed a mass average molecular weight of 220,000 (calculated as polystyrene) and Mw/Mn=1.78. The residue was in a liquid form (paste like) at room temperature.

[Crosslinked Polymer (a-2)]

As the crosslinked polymer (a-2) which is an arbitrary component, the compounds shown in Table 2 below were used.

TABLE 2

| Abbreviation | Kind | Vol. ave. ptcl. diameter | Available from |
|---|---|---|---|
| PMMA-X | polymethyl methacrylate crosslinked polymer | 5 μm | Sekisui Kasei Co., MB30X-5 |

TABLE 2-continued

| Abbreviation | Kind | Vol. ave. ptcl. diameter | Available from |
|---|---|---|---|
| PBMA-X | polybutyl methacrylate crosslinked polymer | 5 μm | Sekisui Kasei Co., BM30X-5 |

[High-Tg Non-Crosslinked Polymer (a-3)]

As the high-Tg non-crosslinked polymer (a-3) which is an arbitrary component, a polymethyl methacrylate having a mass average molecular weight of 200,000 and an average particle size of 0.1 μm (MP1451, manufactured by Soken Chemical & Engineering Co.) was used. This polymer is hereinafter abbreviated as PMMA.

[Inorganic Powder (a-4)]

As the inorganic powder (a-4) which is an arbitrary component, the materials shown in Table 3 below were used.

TABLE 3

| Abbreviation | Composition* | Available from |
|---|---|---|
| Silica | $SiO_2$ | fumed silica "Reolosil MT-10", manufactured by Tokuyama Co. |
| Glass | $SiO_2(55)/BaO(25)/B_2O_3(10)/Al_2O_3(10)$ | dental glass filler "GM27884", manufactured by Schott Co. |
| $CaCO_3$ | $CaCO_3$ | calcium carbonate, manufactured by Wako Junyaku Co. |

*Numerals in parentheses in the glass composition are parts by weight.

2. Liquid Material (b);

[Liquid Polymer]

As the liquid polymer which is the chief component in the liquid material (b) used in Examples and in Comparative Examples, there were used the compounds shown in Table 4 below. These compounds were obtained by polymerizing the corresponding monomers as described in production examples 4 to 8 below.

In Table 4, PBA-5 to PBA-7 are the polymers lying outside the range of oligomer contents and/or mass average molecular weights required by the liquid polymer of the present invention, and are used in Comparative Examples.

TABLE 4

| Abbreviation | Kind | Mass ave. mol. Wt. (Mw) | Mw/Mn | Oligomer content* | Production method |
|---|---|---|---|---|---|
| PPA | poly(propyl acrylate) | 2000 | 1.15 | 5% | production example 4 |
| PEA | poly(ethyl acrylate) | 2000 | 1.20 | 5% | production example 5 |
| PEHA | poly(2-ethylhexyl acrylate) | 2000 | 1.18 | 5% | production example 6 |
| PGA | poly(glycidyl acrylate) | 2000 | 1.18 | 5% | production example 7 |
| PBA-1 | poly(butyl acrylate) | 2000 | 1.15 | 5% | production example 8 |
| PBA-2 | same as above | 6000 | 1.12 | <1% | production example 9 |
| PBA-3 | same as above | 8000 | 1.15 | <1% | production example 10 |
| PBA-4 | same as above | 2000 | 1.35 | 8% | production example 11 |
| PBA-5 | same as above | 2000 | 2.01 | 15% | production example 12 |
| PBA-6 | same as above | 17000 | 1.14 | 0% | production example 13 |
| PBA-7 | same as above | 300 | 1.15 | 95% | production example 14 |

*Oligomer content: ratio of oligomers having mass average molecular weights of not larger than 500 per the whole amount (mass %).

Production Example 4

Synthesis of PPA

Hereinafter, tri(n-butyl) aluminum is abbreviated as TBAl and t-butyl lithium as t-BLi.

A toluene solution of TBAl (TBAl concentration: 1.0 mol/l) and a toluene solution of t-BLi (t-BLi concentration: 1.0 mol/l) were prepared.

3.0 Milliliters of toluene solution of the TBAl (TBAl: 3.0 mmol) and 40 ml of toluene were mixed together, and were cooled at −78° C. 7.4 Milliliters of toluene solution of the above t-BLi (t-BLi: 7.4 mmol) was added to the above mixture, and was stirred for several minutes followed by the careful addition of 14.8 g (130 mmol) of propyl acrylate so that the temperature was not elevated in the reaction system.

The above reaction was conducted in a nitrogen atmosphere using a standard Schlenk flask, and the reagent was migrated by using an injector. Toluene was refluxed on sodium and was, thereafter, distilled off in a nitrogen atmosphere. Propyl acrylate was refined through a basic alumina column and a column of molecular sieves 4A.

The above stirring was conducted for 24 hours and, thereafter, methanol was added thereto to halt the reaction. By using a separating funnel, washing was conducted by using a 50% methanol aqueous solution followed by vacuum drying at 120° C. to obtain 10.2 g of a colorless and transparent liquid polymer (polypropylene acrylate: PPA) (yield, 69%). Through the GPC measurement, it was learned that the liquid polymer possessed a mass average molecular weight of 2,000 (calculated as polystyrene), Mw/Mn=1.15, and contained the components having molecular weights of smaller than 500 in an amount of 5%.

Production Example 5

Synthesis of PEA

By using 2.4 ml of toluene solution of the TBAl (TBAl: 2.4 mmol), 5.9 ml of toluene solution of the t-BLi (t-BLi: 5.9 mmol) and 13.0 g (130 mmol) of ethyl acrylate, the synthesis was conducted by the same method as that of the production example 4 to obtain 8.5 g of a colorless and transparent liquid polymer (polyethyl acrylate: PEA) (yield, 65%). Through the GPC measurement, it was learned that the liquid polymer possessed a mass average molecular weight of 2,000 (calculated as polystyrene), Mw/Mn=1.20, and contained the components having molecular weights of smaller than 500 in an amount of 5%.

Production Example 6

Synthesis of PEHA

By using 4.4 ml of toluene solution of the TBAl (TBAl: 4.4 mmol), 10.9 ml of toluene solution of the t-BLi (t-BLi: 10.9 mmol) and 23.9 g (130 mmol) of 2-ethylhexyl acrylate, the synthesis was conducted by the same method as that of the production example 4 to obtain 16.3 g of a colorless and transparent liquid polymer (poly 2-ethylhexyl acrylate: PEHA) (yield, 68%). Through the GPC measurement, it was learned that the liquid polymer possessed a mass average molecular weight of 2,000 (calculated as polystyrene), Mw/Mn=1.18, and contained the components having molecular weights of smaller than 500 in an amount of 5%.

Production Example 7

Synthesis of PGA

By using 3.0 ml of toluene solution of the TBAl (TBAl: 3.0 mmol), 7.4 ml of toluene solution of the t-BLi (t-BLi: 7.4 mmol) and 16.0 g (126 mmol) of glycidyl acrylate, the synthesis was conducted by the same method as that of the production example 4 to obtain 10.1 g of a colorless and transparent liquid polymer (polyglycidyl acrylate: PGA) (yield, 63%). Through the GPC measurement, it was learned that the liquid polymer possessed a mass average molecular weight of 2,000 (calculated as polystyrene), Mw/Mn=1.18, and contained the components having molecular weights of smaller than 500 in an amount of 5%.

Production Example 8

Synthesis of PBA-1

By using 3.0 ml of toluene solution of the TBAl (TBAl: 3.0 mmol), 7.4 ml of toluene solution of the t-BLi (t-BLi: 7.4 mmol) and 16.1 g (126 mmol) of butyl acrylate, the synthesis was conducted by the same method as that of the production example 4 to obtain 11.6 g of a colorless and transparent liquid polymer (polybutyl acrylate: PBA-1) (yield, 72%). Through the GPC measurement, it was learned that the liquid polymer possessed a mass average molecular weight of 2,000 (calculated as polystyrene), Mw/Mn=1.15, and contained the components having molecular weights of smaller than 500 in an amount of 5%.

Production Example 9

Synthesis of PBA-2

The synthesis was conducted by the same method as that of the production example 4 but using 1.0 ml of toluene solution of the TBAl (TBAl: 1.0 mmol) and 2.5 ml of toluene solution of the t-BLi (t-BLi: 2.5 mmol) to obtain 10.1 g of a colorless and transparent liquid polymer (polybutyl acrylate: PBA-2) (yield, 63%). Through the GPC measurement, it was learned that the liquid polymer possessed a mass average molecular weight of 6,000 (calculated as polystyrene), Mw/Mn=1.12, and contained the components having molecular weights of smaller than 500 in an amount of less than 1%.

Production Example 10

Synthesis of PBA-3

The synthesis was conducted by the same method as that of the production example 8 but using 0.76 ml of toluene solution of the TBAl (TBAl: 0.76 mmol) and 1.9 ml of toluene solution of the t-BLi (t-BLi: 1.9 mmol) to obtain 10.9 g of a colorless and transparent liquid polymer (polybutyl acrylate: PBA-3) (yield, 68%). Through the GPC measurement, it was learned that the liquid polymer possessed a mass average molecular weight of 8,000 (calculated as polystyrene), Mw/Mn=1.15, and contained the components having molecular weights of smaller than 500 in an amount of less than 1%.

Production Example 11

PBA-4

A toluene solution (n-BLi concentration: 1.0 mmol/l) of n-butyl lithium (abbreviated as n-BLi) was prepared.

The synthesis was conducted by the same method as that of the production example 8 but using 8.0 ml of toluene solution of the n-BLi (n-BLi: 8.0 mmol) instead of using the toluene solution of t-BLi to obtain 9.6 g of a colorless and transparent liquid polymer (polybutyl acrylate: PBA-4) (yield, 60%). Through the GPC measurement, it was learned that the liquid polymer possessed a mass average molecular weight of 2,000 (calculated as polystyrene), Mw/Mn=1.35, and contained the components having molecular weights of smaller than 500 in an amount of 8%.

Production Example 12

Synthesis of PBA-5

Into a three neck distillation flask were introduced 12.8 g (100 mmol) of butyl acrylate, 2.0 g AIBN and 100 ml of toluene, and a nitrogen gas was continuously flown at a rate of 5 ml/min. for 2 hours. After the flow of the nitrogen gas was discontinued, an oil bath was attached and the stirring was continued at a bath temperature of 70° C. for 2 hours while paying attention so that no gushing took place. By using a separating funnel, washing was conducted by using a 50% methanol aqueous solution followed by vacuum drying at 120° C. to obtain 4.6 g of a colorless and transparent liquid polymer (polybutyl acrylate: PBA-5) (yield, 36%). Through the GPC measurement, it was learned that the liquid polymer possessed a mass average molecular weight of 2,000 (calculated as polystyrene), Mw/Mn=2.01, and contained the components having molecular weights of smaller than 500 in an amount of 15%.

Production Example 13

Synthesis of PBA-6

The synthesis was conducted by the same method as that of the production example 8 but using 50 μml of toluene solution of the TBAl (TBAl: 50 mmol) and 124 μml of toluene solution of the t-BLi (t-BLi: 124 mmol) to obtain 12.3 g of a colorless and transparent liquid polymer (polybutyl acrylate: PBA-6) (yield, 76%). Through the GPC measurement, it was learned that the liquid polymer possessed a mass average molecular weight of 17,000 (calculated as polystyrene), Mw/Mn=1.14, and contained no component having a molecular weight of smaller than 500.

Production Example 14

Synthesis of PBA-7

The synthesis was conducted by the same method as that of the production example 8 but using 20 ml of toluene solution of the TBAl (TBAl: 20 mmol) and 50 ml of toluene solution of the t-BLi (t-BLi: 50 mmol) to obtain 8.7 g of a colorless and transparent liquid polymer (polybutyl acrylate: PBA-7) (yield, 54%). Through the GPC measurement, it was learned that the liquid polymer possessed a mass average molecular weight of 300 (calculated as polystyrene), Mw/Mn=1.15, and contained components having molecular weights of smaller than 500 in an amount of 95%.

3. Adhesive;

The following adhesives were used for adhering the tissue conditioner to the (meth)acrylic denture base in Examples and in Comparative Examples. Each adhesive contained a polymer at a concentration of 5 mass %. The copolymers (or homopolymers) used for preparing the adhesives were those produced by the following production examples 15 to 27.

Abbreviations used in the column of constituent monomers in Table 5 below and in the following production examples 15 to 27 stand for the following (meth)acrylate monomers.

MMA: methyl methacrylate

BMA: n-butyl methacrylate

EHMA: 2-ethylhexyl methacrylate i-BMA: i-butyl methacrylate

OMA: n-octyl methacrylate

ODMA: n-octadecyl methacrylate

BA: n-butyl acrylate

EMA: ethyl methacrylate

TABLE 5

| Abbreviation | Copolymer* Constituent monomer | | | Ratio | Mw. | Mw/Mn | Copolymer is obtained from | Organic solvent |
|---|---|---|---|---|---|---|---|---|
| A1-1 | MMA | BMA | — | 30:70 | 180,000 | 2.10 | Production. Ex. 15 | ethyl acetate |
| A1-2 | | | | same as above | | | | acetone |
| A2 | MMA | EHMA | — | 30:70 | 180,000 | 2.12 | Production. Ex. 16 | ethyl acetate |
| A3 | MMA | i-BMA | — | 30:70 | 180,000 | 2.22 | Production. Ex. 17 | ethyl acetate |
| A4 | MMA | OMA | — | 30:70 | 180,000 | 2.25 | Production. Ex. 18 | ethyl acetate |
| A5 | MMA | ODMA | — | 30:70 | 180,000 | 2.20 | Production. Ex. 19 | ethyl acetate |
| A6 | MMA | BMA | i-BMA | 20:40:40 | 180,000 | 2.30 | Production. Ex. 20 | ethyl acetate |
| A7 | MMA | BA | — | 30:70 | 180,000 | 2.32 | Production. Ex. 21 | ethyl acetate |
| A8 | MMA | BMA | — | 50:50 | 180,000 | 2.15 | Production. Ex. 22 | ethyl acetate |
| A9 | MMA | BMA | — | 70:30 | 180,000 | 2.12 | Production. Ex. 23 | ethyl acetate |
| A10 | MMA | BMA | — | 30:70 | 500,000 | 1.65 | Production. Ex. 24 | ethyl acetate |
| B1 | MMA | — | — | — | 180,000 | 2.15 | Production. Ex. 25 | ethyl acetate |
| B2 | — | BMA | — | — | 180,000 | 2.20 | Production. Ex. 26 | ethyl acetate |
| B3 | — | EMA | — | — | 180,000 | 2.15 | Production. Ex. 27 | ethyl acetate |

*The concentration in the adhesive is 5 mass % (copolymer/solvent = 5/95).

Production Example 15

Production of a Copolymer Used for the Adhesives A1-1 and A1-2

Into a three neck distillation flask were introduced:

3.0 g (30 mmol) of MMA, 10.0 g (70 mmol) of BMA, 0.02 g of AIBN and 10 ml of toluene, and a nitrogen gas was continuously flown at a rate of 5 ml/min. for 2 hours. After the flow of the nitrogen gas was discontinued, an oil bath was attached and the stirring was continued at a bath temperature of 70° C. for 6 hours. Next, the reaction product was introduced into 10 times amount of methanol, and the formed precipitate was recovered and was washed with methanol. The obtained precipitate was dissolved in benzene, freeze dried, and 8.6 g of an MMA/BMA copolymer (copolymerizing ratio of 30:70) was obtained (yield, 66%). Through the GPC measurement, it was learned that the above copolymer possessed a mass average molecular weight of 180,000 (calculated as polystyrene) and Mw/Mn=2.10.

Production Example 16

Production of a Copolymer Used for the Adhesive A2

The synthesis was carried out in the same manner as in the production example 15 but using 13.9 g (70 mmol) of EHMA instead of BMA, and 11.5 g of an MMA/EHMA copolymer (copolymerizing ratio of 30:70) was obtained (yield, 68%). Through the GPC measurement, it was learned that the above copolymer possessed a mass average molecular weight of 180,000 (calculated as polystyrene) and $Mw/Mn=2.12$.

Production Example 17

Production of a Copolymer Used for the Adhesive A3

The synthesis was carried out in the same manner as in the production example 15 but using 10.0 g (70 mmol) of i-BMA instead of BMA, and 8.0 g of an MMA/1-BMA copolymer (copolymerizing ratio of 30:70) was obtained (yield, 62%). Through the GPC measurement, it was learned that the above copolymer possessed a mass average molecular weight of 180,000 (calculated as polystyrene) and $Mw/Mn=2.22$.

Production Example 18

Production of a Copolymer Used for the Adhesive A4

The synthesis was carried out in the same manner as in the production example 15 but using 13.9 g (70 mmol) of OMA instead of BMA, and 10.5 g of an MMA/OMA copolymer (copolymerizing ratio of 30:70) was obtained (yield, 62%). Through the GPC measurement, it was learned that the above copolymer possessed a mass average molecular weight of 180,000 (calculated as polystyrene) and $Mw/Mn=2.25$.

Production Example 19

Production of a Copolymer Used for the Adhesive A5

The synthesis was carried out in the same manner as in the production example 15 but using 23.7 g (70 mmol) of ODMA instead of BMA, and 18.7 g of an MMA/ODMA copolymer (copolymerizing ratio of 30:70) was obtained (yield, 70%). Through the GPC measurement, it was learned that the above copolymer possessed a mass average molecular weight of 180,000 (calculated as polystyrene) and $Mw/Mn=2.20$.

Production Example 20

Production of a Copolymer Used for the Adhesive A6

Into a three neck distillation flask were introduced:
2.0 g (20 mmol) of MMA, 5.1 g (40 mmol) of BMA, 5.1 g (40 mmol) of i-BMA, 0.02 g of AIBN and 10 ml of toluene, and the synthesis was carried out in the same manner as in the production example 15.

As a result, 6.1 g of an MMA/BMA/1-BMA copolymer (copolymerizing ratio of 20:40:40) was obtained (yield, 50%). Through the GPC measurement, it was learned that the above copolymer possessed a mass average molecular weight of 180,000 (calculated as polystyrene) and $Mw/Mn=2.30$.

Production Example 21

Production of a Copolymer Used for the Adhesive A7

The synthesis was carried out in the same manner as in the production example 15 but using 12.8 g (100 mmol) of BA instead of BMA, and 7.2 g of an MMA/BA copolymer (copolymerizing ratio of 30:70) was obtained (yield, 46%). Through the GPC measurement, it was learned that the above copolymer possessed a mass average molecular weight of 180,000 (calculated as polystyrene) and $Mw/Mn=2.32$.

Production Example 22

Production of a Copolymer Used for the Adhesive A8

The synthesis was carried out in the same manner as in the production example 15 but using 5.0 g (50 mmol) of MMA and 6.4 g (50 mmol) of BMA. As a result, 7.4 g of an MMA/BMA copolymer (copolymerizing ratio of 50:50) was obtained (yield, 65%). Through the GPC measurement, it was learned that the above copolymer possessed a mass average molecular weight of 180,000 (calculated as polystyrene) and $Mw/Mn=2.15$.

Production Example 23

Production of a Copolymer Used for the Adhesive A9

The synthesis was carried out in the same manner as in the production example 15 but using 7.0 g (70 mmol) of MMA and 3.8 g (30 mmol) of BMA. As a result, 7.1 g of an MMA/BMA copolymer (copolymerizing ratio of 70:30) was obtained (yield, 66%). Through the GPC measurement, it was learned that the above copolymer possessed a mass average molecular weight of 180,000 (calculated as polystyrene) and $Mw/Mn=2.12$.

Production Example 24

Production of a Copolymer Used for the Adhesive A10

Into a four neck distillation flask were introduced:
3.0 g (30 mmol) of MMA, 10.0 g (70 mmol) of BMA, 0.01 g of AIBN, 15 ml of water, 0.14 g of polyoxyethylenenonylphenyl ether and 0.14 g of laurylamine acetate, and a nitrogen gas was continuously flown at a rate of 5 ml/min. for 2 hours. After the flow of the nitrogen gas was discontinued, an oil bath was attached and the stirring was continued at a bath temperature of 70° C. for 6 hours. After the reaction, the emulsion was frozen to isolate the polymer. The thus obtained polymer was introduced into 10 times amount of methanol, and the formed precipitate was recovered and was washed with methanol. The obtained precipitate was dissolved in benzene, freeze dried, and 8.6 g of an MMA/BMA copolymer (copolymerizing ratio of 30:70) was obtained (yield, 66%). Through the GPC measurement, it was learned that the above copolymer possessed a mass average molecular weight of 500,000 (calculated as polystyrene) and $Mw/Mn=1.65$.

Production Example 25

Production of a Copolymer Used for the Adhesive B1

Into a three neck distillation flask were introduced:
10.0 g (100 mmol) of MMA, 0.02 g of AIBN and 10 ml of toluene, and a nitrogen gas was continuously flown at a rate of 5 ml/min. for 2 hours. After the flow of the nitrogen gas was discontinued, an oil bath was attached and the stirring was continued at a bath temperature of 70° C. for 6 hours. The obtained reaction product was introduced into 10 times amount of methanol, and the formed precipitate was recovered and was washed with methanol. The obtained precipitate was dissolved in benzene, freeze dried, and 7.1 g of an MMA homopolymer was obtained (yield, 71%). Through the GPC measurement, it was learned that the above homopolymer possessed a mass average molecular weight of 180,000 (calculated as polystyrene) and Mw/Mn=2.15.

Production Example 26

Production of a Copolymer Used for the Adhesive B2

Into a three neck distillation flask were introduced:
14.3 g (100 mmol) of MBA, 0.02 g of AIBN and 10 ml of toluene, and a nitrogen gas was continuously flown at a rate of 5 ml/min. for 2 hours. After the flow of the nitrogen gas was discontinued, an oil bath was attached and the stirring was continued at a bath temperature of 70° C. for 6 hours. Next, the reaction product was introduced into 10 times amount of methanol, and the formed precipitate was recovered and was washed with methanol. The obtained precipitate was dissolved in benzene, freeze dried, and 8.7 g of a BMA homopolymer was obtained (yield, 61%). Through the GPC measurement, it was learned that the above homopolymer possessed a mass average molecular weight of 180,000 (calculated as polystyrene) and Mw/Mn=2.20.

Production Example 27

Production of a Copolymer Used for the Adhesive B3

Into a three neck distillation flask were introduced:
11.4 g (100 mmol) of EMA, 0.02 g of AIBN and 10 ml of toluene, and a nitrogen gas was continuously flown at a rate of 5 ml/min. for 2 hours. After the flow of the nitrogen gas was discontinued, an oil bath was attached and the stirring was continued at a bath temperature of 70° C. for 6 hours. Next, the reaction product was introduced into 10 times amount of methanol, and the formed precipitate was recovered and was washed with methanol. The obtained precipitate was dissolved in benzene, freeze dried, and 6.8 g of an EMA homopolymer was obtained (yield, 60%). Through the GPC measurement, it was learned that the above homopolymer possessed a mass average molecular weight of 180,000 (calculated as polystyrene) and Mw/Mn=2.15.

Example 1

Use was made of a PBMA powder (see Table 1 for its properties) which is a non-crosslinked polymer having Tg of 20° C. as the powdery material and PPA which is a liquid polymer having a mass average molecular weight (Mw) of 2,000 and an oligomer content of 5 mass % as the liquid material. The powdery material and the liquid material were used in combination as the tissue conditioner. The evaluated results of the tissue conditioner were as shown in Table 6. In preparing a paste of the tissue conditioner, the powdery material and the liquid material were used at a ratio of powder/liquid=1.1 (mass ratio).

Examples 2 to 9 and Comparative Example 1

The tissue conditioners were prepared by using liquid polymers shown in Table 6 as the liquid materials in combination with the PBMA powder, and were evaluated in the same manner as in Example 1. The evaluated results were as shown in Table 6.

Comparative Example 2

The tissue conditioner was prepared by using the liquid polymer which was the PBA-6 having a mass average molecular weight of 17,000 as the liquid material in combination with the PBMA powder, and was evaluated in the same manner as in Example 1. The results were as shown in Table 6. Here, it was attempted to mix the powdery material (PBMA powder) and the liquid material together and knead them together. However, the viscosity of the liquid material was so high that a homogeneous mixture (paste) could not be obtained through the kneading by hand.

TABLE 6

| | Tissue conditioner composition*[1] | | | | |
|---|---|---|---|---|---|
| | Powder | Liquid | | | Compatibility, |
| | Kind | Kind | (Mw) | Oligomer content | viscosity (Pa s) |
| Ex. 1 | PBMA | PPA | (2000) | (5 wt %) | 4500 |
| Ex. 2 | same as above | PEA | (2000) | (5 wt %) | 4000 |
| Ex. 3 | same as above | PEHA | (2000) | (5 wt %) | 4500 |
| Ex. 4 | same as above | PGA | (2000) | (5 wt %) | 4800 |
| Ex. 5 | same as above | PBA-1 | (2000) | (5 wt %) | 6000 |
| Ex. 6 | same as above | PBA-2 | (6000) | (<1 wt %) | 5200 |
| Ex. 7 | same as above | PBA-3 | (8000) | (<1 wt %) | 4600 |
| Ex. 8 | same as above | PBA-4 | (2000) | (8 wt %) | 5300 |
| Ex. 9 | same as above | PBA-1 | (2000) | (5 wt %) | 5000 |
| | | PEA*[2] | (2000) | (5 wt %) | |
| Comp. Ex. 1 | same as above | PBA-5 | (2000) | (15 wt %) | 4500 |
| Comp. Ex. 2 | same as above | PBA-6 | (17000) | (0 wt %) | *[3] |

TABLE 6-continued

|  | Kneading time (sec) | Initial viscosity (Pa s) | Hardness (Shore A) | | Flexural strength of denture base (MPa) | |
| --- | --- | --- | --- | --- | --- | --- |
|  |  |  | Initially | One month after | Initially | One month after |
| Ex. 1 | 90 | 90 | 11 | 11 | 120 | 114 |
| Ex. 2 | 90 | 90 | 15 | 15 | 120 | 112 |
| Ex. 3 | 90 | 90 | 13 | 13 | 120 | 119 |
| Ex. 4 | 90 | 90 | 12 | 12 | 120 | 118 |
| Ex. 5 | 90 | 90 | 10 | 10 | 120 | 118 |
| Ex. 6 | 100 | 95 | 10 | 10 | 120 | 120 |
| Ex. 7 | 100 | 100 | 11 | 11 | 120 | 120 |
| Ex. 8 | 90 | 80 | 11 | 15 | 120 | 116 |
| Ex. 9 | 90 | 90 | 11 | 11 | 120 | 117 |
| Comp. Ex. 1 | 90 | 85 | 10 | 23 | 120 | 115 |
| Comp. Ex. 2 | difficult to mix powder and liquid together | | | | | |

*[1]Mixing ratio of powder/liquid = 1.1 (mass ratio).
*[2]Mixture of PBA-1 and PEA in equal amounts.
*[3]difficult to mix powder and liquid together As will be understood from the results of Table 6, the tissue conditioners of Examples 1 to 9 of the present invention all have initial hardnesses of not larger than 20, which are favorable values for the tissue conditioners and, besides, do not almost permit the hardnesses to change even after the passage of one month which is a period in which the tissue conditioners are usually used. In particular, the tissue conditioners (Examples 1 to 7) obtained by using liquid polymers containing oligomers of molecular weights of not larger than 500 in amounts of less than 7 mass % as liquid materials, exhibit superior properties to those of the tissue conditioner (Example 8) that uses the liquid polymer containing oligomers in amounts larger than the above amount, as the liquid material.

When the liquid polymer having the oligomer content of 15 mass % is used (Comparative Example 1), the hardness of the paste becomes 2.3 times as high as the initial hardness one month after. Therefore, the tissue conditioner of this composition must be lined again frequently. Further, when the liquid polymer having a low oligomer content but having a high average molecular weight is used (Comparative Example 2), it becomes difficult to mix the powdery material and the liquid material together, which, therefore, cannot be used as the dental tissue conditioner.

Further, as will be understood from the comparison of Example 5 with Examples 6, 7, the kneading time until the homogeneity is attained becomes short when the liquid polymer has a low mass average molecular weight. In this case, the kneaded product, too, has a low viscosity and offers excellent operability.

Comparative Example 3

The tissue conditioner was prepared and evaluated in the same manner as in Example 1 but using, as the powdery material, a non-cross-linked PEMA powder having Tg of 65° C. and a liquid polymer as the liquid material. The evaluated results are shown in Table 7 together with the results of Example 1. In this case, the paste exhibited too high initial hardness and could not be used as the tissue conditioner.

Comparative Example 4

It was attempted to use the non-crosslinked POMA having Tg of −20° C. as the powdery material. As described in the production example 3 above, however, the polymer remained to be a paste at room temperature, and the powdery material could not be obtained therefrom.

TABLE 7

| Tissue conditioner composition*[1] | | | Kneading time (sec) | Initial viscosity (Pa s) | Hardness (Shore A) | | Flexural strength of denture base (MPa) | | Ave. ptcl. size of powder (μm) | |
| --- | --- | --- | --- | --- | --- | --- | --- | --- | --- | --- |
| Powder | | Liquid | | | | | | | | |
| Kind | (Tg) | Kind | | | Initially | One month after | Initially | One month after | Initially | Three months after |
| Ex. 1 | PBMA | (20° C.) | PPA | 90 | 90 | 11 | 11 | 120 | 114 | 40 | 120 |
| Comp. Ex. 3 | PEMA | (65° C.) | PPA | 120 | 90 | 23 | 25 | 120 | 119 | 35 | 36 |
| Comp. Ex. 4 | POMA | (−20° C.) | — | Powder could not be obtained | | | | | | | |

*[1]Mixing ratio of powder/liquid = 1.1 (mass ratio).

Examples 10 to 12

Tissue conditioners were prepared by using in combination PBA-1 (liquid polymer) having a mass average molecular weight of 2,000 and an oligomer content of 5 mass % as the liquid material and non-crosslinked polymer powders shown in Table 8 as powdery materials. Like in Example 1, these materials were mixed at a mass ratio of powdery material/liquid material=1.1 to prepare pastes of tissue conditioners which were, then, evaluated. Table 8 shows the results of evaluation together with the results of Example 5 above.

TABLE 8

| | Tissue conditioner composition*[1] | | | Kneading time (sec) | Initial viscosity (Pa s) | Hardness (Shore A) | | Flexural strength of denture base (MPa) | | Ave. ptcl. size of powder (μm) | |
|---|---|---|---|---|---|---|---|---|---|---|---|
| | Powder | | Liquid | | | | One month | | One month | | Three months |
| | Kind | (Tg) | Kind | | | Initially | after | Initially | after | Initially | after |
| Ex. 5 | PBMA | (20° C.) | PBA-1 | 90 | 90 | 10 | 10 | 120 | 118 | 40 | 120 |
| Ex. 10 | PiBMA | (56° C.) | same as above | 90 | 80 | 18 | 19 | 120 | 116 | 90 | 113 |
| Ex. 11 | PHDMA | (15° C.) | same as above | 90 | 90 | 9 | 9 | 120 | 118 | 80 | 170 |
| Ex. 12 | PTMHMA | (5° C.) | same as above | 90 | 90 | 6 | 7 | 120 | 115 | 80 | 198 |

*[1]Mixing ratio of powder/liquid = 1.1 (mass ratio).

Example 13

Use was made of the PBMA powder which is a non-crosslinked polymer having Tg of 20° C. as the powdery material and a mixed solution of 100 parts by mass of PBA-1 which is a liquid polymer and 10 parts by mass of an isopropyl alcohol (organic solvent, IPA) as the liquid material. The powdery material and the liquid material were used in combination as the tissue conditioner. Like in Example 1, these materials were mixed at a mass ratio of powdery material/liquid material=1.1 to prepare a paste of the tissue conditioner which was, then, evaluated. Table 9 shows the results thereof.

Examples 14 to 17

Pastes of tissue conditioners were prepared and evaluated in the same manner as in Example 13 but varying the kinds and amounts of the organic solvents blended in the liquid material. The results were as shown in Table 9.

TABLE 9

| | | Tissue conditioner composition*[1] | | | | | | | Hardness (Shore A) | | Flexural strength of denture base (MPa) | |
|---|---|---|---|---|---|---|---|---|---|---|---|---|
| | | Liquid | | | | | | | | | | |
| | | Liquid polymer | | | | Org. solvent | | Kneading time (sec) | Initial viscosity (Pa s) | | One month | One month |
| | Powder Kind | Kind | (Mw) | (Oligomer content) | Blended amount*[2] | Kind | Blended amount*[2] | | | Initially | after | Initially | after |
| Ex. 13 | PBMA | PBA-1 | (2000) | (5 wt %) | 100 | IPA | 10 | 30 | 100 | 11 | 11 | 120 | 116 |
| Ex. 14 | same as above | same as above | | | 100 | acetone | 10 | 30 | 100 | 10 | 10 | 120 | 113 |
| Ex. 15 | same as above | same as above | | | 100 | isobutyl alcohol | 10 | 40 | 100 | 10 | 10 | 120 | 117 |
| Ex. 16 | same as above | same as above | | | 100 | ethanol | 5 | 50 | 95 | 8 | 8 | 120 | 119 |
| Ex. 17 | same as above | same as above | | | 100 | ethanol | 20 | 20 | 110 | 12 | 13 | 120 | 115 |
| Comp. Ex. 5 | same as above | PBA-7 | (300) | (95 wt %) | 100 | ethanol | 20 | 80 | 80 | 10 | 40 | 120 | 114 |

TABLE 9-continued

| | | Tissue conditioner composition*[1] | | | | | | | Hardness (Shore A) | | Flexural strength of denture base (MPa) | |
|---|---|---|---|---|---|---|---|---|---|---|---|---|
| | | Liquid | | | | | | | | | | |
| | | Liquid polymer | | | Org. solvent | | Kneading time (sec) | Initial viscosity (Pa·s) | | One month | | One month |
| | Powder Kind | Kind | (Mw) | (Oligomer content) | Blended amount*[2] | Kind | Blended amount*[2] | | | Initially | after | Initially | after |
| Comp. Ex. 6 | same as above | (2-ethylhexyl sebacate) | | | 100 | ethanol | 10 | 30 | 30 | 10 | 50 | 120 | 60 |
| Comp. Ex. 7 | same as above | (2-ethylhexyl phthalate) | | | 100 | ethanol | 10 | 30 | 30 | 10 | 50 | 120 | 55 |

*[1]Mixing ratio of powder/liquid = 1.1 (mass ratio).
*[2]Parts by mass.

As shown in Table 9, by using a mixed solution obtained by blending the liquid polymer with a small amount of water-soluble organic solvent as the liquid material, the kneading time can be greatly shortened as compared to when no water-soluble organic solvent is blended (e.g., Example 5), and the tissue conditioner having further improved operability is obtained. Further, even by being blended with the water-soluble organic solvent, it will be understood that other properties are not almost affected.

Comparative Example 5

A tissue conditioner was prepared and evaluated in the same manner as in Example 13 but using a mixed solution of 100 parts by mass of PBA-7 (liquid polymer) having a mass average molecular weight of 300 (content of oligomers having molecular weights of not larger than 500:95 mass %) and 20 parts by mass of ethanol. The results were as shown in Table 9. The paste exhibited a favorable initial hardness. After one month has passed, however, the paste exhibited a very increased hardness. This is presumably due to that the liquid polymer has a small molecular weight and elutes out with the passage of time.

Comparative Examples 6 and 7

Tissue conditioners were prepared and evaluated in the same manner as in Example 13 but using mixed solutions of 100 parts by mass of a sebacic acid ester (2-ethylhexyl sebacate: molecular weight 427) or a phthalic acid ester (2-ethylhexyl phthalate: molecular weight 391) that has heretofore been used as a plasticizer in the tissue conditioner as the liquid material and 10 parts by mass of ethanol. The results were as shown in Table 9. In this case, too, the paste exhibited a very increased hardness after one month has passed and, besides, flexural strength of the denture base (acrylic plate) was nearly halved.

Examples 18 to 27

Tissue conditioners were prepared by using in combination the powdery materials and the liquid materials of compositions shown in Table 10. These materials were mixed at a mass ratio of powdery material/liquid material=1.1 to prepare pastes of tissue conditioners which were, then, evaluated. Table 11 shows the results.

TABLE 10

| | Tissue conditioner composition*[1] | | | | | | | | | | | |
|---|---|---|---|---|---|---|---|---|---|---|---|---|
| | Powder | | | | | | | | Liquid | | | |
| | Low-Tg non-crosslinked polymer | | crosslinked polymer | | High-Tg non-crosslinked | | Inorganic powder | | Liquid polymer | | Org. solvent | |
| | Kind | Blended amount*[2] | Kind | Blended amount*[2] | Kind | Blended amount*[2] | Kind | Blended amount*[2] | Kind | Blended amount*[2] | Kind | Blended amount*[2] |
| Ex. 18 | PBMA | 100 | PMMA-X | 80 | — | — | — | — | PBA-1 | 100 | — | — |
| Ex. 19 | same as above | 100 | same as above | 20 | — | — | — | — | same as above | | — | — |
| Ex. 20 | same as above | 100 | PBMA-X | 80 | — | — | — | — | same as above | | — | — |
| Ex. 21 | same as above | 100 | — | — | PMMA | 5 | — | — | same as above | | — | — |
| Ex. 22 | same as above | 100 | — | — | — | — | silica | 1 | same as above | | — | — |
| Ex. 23 | same as above | 100 | — | — | — | — | silica | 0.1 | same as above | | — | — |
| Ex. 24 | same as above | 100 | — | — | — | — | glass | 1 | same as above | | — | — |
| Ex. 25 | same as above | 100 | — | — | — | — | CaCO$_3$ | 1 | same as above | | — | — |
| Ex. 26 | same as above | 100 | PBMA-X | 80 | PMMA | 5 | silica | 1 | same as above | | — | — |

TABLE 10-continued

Tissue conditioner composition[*1]

| | Powder | | | | | | | | | | Liquid | | |
|---|---|---|---|---|---|---|---|---|---|---|---|---|---|
| | Low-Tg non-crosslinked polymer | | crosslinked polymer | | High-Tg non-crosslinked | | Inorganic powder | | Liquid polymer | | Org. solvent | | |
| Kind | Blended amount[*2] | Kind | Blended amount[*2] | Kind | Blended amount[*2] | Kind | Blended amount[*2] | Kind | Blended amount[*2] | Kind | Blended amount[*2] |
| Ex. 27 | | | | same as above | | | | | PBA-1 | 100 | ethanol | 5 |

[*1]Mixing ratio of powder/liquid = 1.1 (mass ratio).
[*2]Parts by mass.
—: no blend

TABLE 11

Evaluated results

| | Kneading time (sec) | Initial viscosity (Pa s) | Hardness (Shore A) | | Flexural strength of denture base (MPa) | | Ave. ptcl. size of powdery material (μm) | |
|---|---|---|---|---|---|---|---|---|
| | | | Initially | One month after | Initially | One month after | Initially | Three month after |
| Ex. 18 | 80 | 20 | 10 | 10 | 120 | 118 | 25 | 105 |
| Ex. 19 | 90 | 50 | 10 | 10 | 120 | 118 | 35 | 115 |
| Ex. 20 | 80 | 20 | 10 | 10 | 120 | 118 | 25 | 95 |
| Ex. 21 | 90 | 90 | 10 | 10 | 120 | 120 | 38 | 40 |
| Ex. 22 | 110 | 100 | 14 | 15 | 120 | 119 | 40 | 80 |
| Ex. 23 | 100 | 95 | 12 | 12 | 120 | 117 | 40 | 96 |
| Ex. 24 | 110 | 100 | 15 | 15 | 120 | 115 | 40 | 100 |
| Ex. 25 | 110 | 95 | 14 | 14 | 120 | 116 | 40 | 98 |
| Ex. 26 | 80 | 30 | 14 | 14 | 120 | 116 | 24 | 25 |
| Ex. 27 | 20 | 30 | 14 | 14 | 120 | 120 | 24 | 26 |

As will be understood from Tables 10 and 11, by using a crosslinked polymer in combination with a non-crosslinked polymer as the powdery material (Examples 18 to 20, 26 and 27), the initial viscosity decreases as compared to when the crosslinked polymer is not used in combination (Example 5), and pastes of tissue conditioners can be prepared featuring further improved operability.

As demonstrated in Examples 21, 26 and 27, further, by using a high-Tg polymer in combination with a low-Tg non-crosslinked polymer as the powdery material, a change in the average particle size can be decreased even after the powdery material is preserved. This avoids such a problem that the operation feeling of the paste varies after the powdery material is preserved for extended periods of time.

As demonstrated in Examples 22 to 25, further, when the compositions blended with small amounts of inorganic powdery material are used as the powdery materials, it becomes possible to increase the final hardness of the pastes and, therefore, to finely adjust the properties with ease. Further, a change in the particle size of the powdery materials can be suppressed to some extent by blending an inorganic powder.

Example 28

By using the same tissue conditioner as the one of Example 5 and by using the adhesive A1-1 described above, the adhesion was evaluated. The results were as shown in Table 12.

Examples 29 to 44 and Reference Examples 1 to 4

The adhesion was evaluated by varying the tissue conditioner and the adhesive as shown in Table 12. The results were as shown in Table 12.

TABLE 12

| | | | Evaluation of adhesion | |
|---|---|---|---|---|
| | Tissue conditioner | Adhesive | Initially | One month after |
| Ex. 28 | composition of Ex. 5 | A1-1 | A | A |
| Ex. 29 | same as above | A1-2 | A | A |
| Ex. 30 | same as above | A2 | A | A |
| Ex. 31 | same as above | A3 | A | A |
| Ex. 32 | same as above | A4 | A | A |
| Ex. 33 | same as above | A5 | A | A |
| Ex. 34 | same as above | A6 | A | A |
| Ex. 35 | same as above | A7 | A | A |
| Ex. 36 | same as above | A8 | A | A |
| Ex. 37 | same as above | A9 | A | A |
| Ex. 38 | same as above | A10 | A | A |
| Ex. 39 | composition of Ex. 9 | A1-1 | A | A |
| Ex. 40 | composition of Ex. 13 | same as above | A | A |
| Ex. 41 | composition of Ex. 18 | same as above | A | A |
| Ex. 42 | composition of Ex. 21 | same as above | A | A |

TABLE 12-continued

|  | Tissue conditioner | Adhesive | Evaluation of adhesion | |
|---|---|---|---|---|
|  |  |  | Initially | One month after |
| Ex. 43 | composition of Ex. 26 | same as above | A | A |
| Ex. 44 | composition of Ex. 27 | same as above | A | A |
| Ref. Ex. 1 | composition of Ex. 26 | none | C | C |
| Ref. Ex. 2 | same as above | B1 | C | C |
| Ref. Ex. 3 | same as above | B2 | C | C |
| Ref. Ex. 4 | same as above | B3 | C | C |

From the results of evaluation of Table 12, it will be learned that to adhere the tissue conditioner of the invention to the methacrylic denture base, it is desired to use, as an adhesive, a solution that contains a copolymer of a methyl(meth)acrylate and a (meth)acrylate of alcohols having 3 to 20 carbon atoms, and an organic solvent.

The invention claimed is:

1. A tissue conditioner for dental use comprising (a) a powdery material and (b) a liquid material which are packed separately from each other and which, at the time of use, are mixed together so as to be used as a paste thereof, wherein:
the powdery material (a) is a non-crosslinked (meth)acrylic polymer powder having a glass transition temperature in a range of 0 to 60° C.; and
the liquid material (b) is a (meth)acrylic polymer having a (meth)acrylic unit as a recurring unit, having a mass average molecular weight in a range of 1,200 to 7,000 and containing not more than 10 mass % of oligomers having molecular weights of not more than 500.

2. The tissue conditioner according to claim 1, wherein said liquid material (b) further contains a water-soluble organic solvent.

3. The tissue conditioner according to claim 1, wherein said powdery material (a) further contains a crosslinked polymer powder.

4. The tissue conditioner according to claim 1, wherein said powdery material (a) further contains another non-crosslinked polymer powder having a glass transition temperature which is not lower than 60° C. and volume average particle size of not larger than 1 µm.

5. The tissue conditioner according to claim 1, wherein said powdery material (a) further contains a crosslinked polymer powder and another non-crosslinked polymer powder having a glass transition temperature which is not lower than 60° C. and volume average particle size of not larger than 1 µm.

6. The tissue conditioner according to claim 1, wherein said powdery material (a) further contains an inorganic powder.

7. A tissue conditioner kit for dental use comprising the tissue conditioner for dental use of claim 1, and a liquid adhesive, said liquid adhesive containing a copolymer of a methyl methacrylate and a (meth)acrylate of alcohols with 3 to 20 carbon atoms, and an organic solvent.

* * * * *